(12) United States Patent
Lee et al.

(10) Patent No.: US 9,045,419 B2
(45) Date of Patent: Jun. 2, 2015

(54) CONDENSED-CYCLIC COMPOUND AND ORGANIC LIGHT EMITTING DIODE HAVING ORGANIC LAYER INCLUDING THE SAME

(75) Inventors: Kwan-Hee Lee, Yongin (KR);
Mi-Kyung Kim, Yongin (KR);
Seung-Gak Yang, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 286 days.

(21) Appl. No.: 12/853,224

(22) Filed: Aug. 9, 2010

(65) Prior Publication Data

US 2011/0031484 A1    Feb. 10, 2011

(30) Foreign Application Priority Data

Aug. 10, 2009    (KR) .................. 10-2009-0073522

(51) Int. Cl.
| | | |
|---|---|---|
| H01L 51/54 | (2006.01) | |
| C09K 11/06 | (2006.01) | |
| C07D 487/04 | (2006.01) | |
| C07D 209/86 | (2006.01) | |
| C07D 401/10 | (2006.01) | |
| C07D 209/90 | (2006.01) | |
| H01L 51/00 | (2006.01) | |
| C07D 403/10 | (2006.01) | |
| H01L 51/50 | (2006.01) | |

(52) U.S. Cl.
CPC .............. *C07D 209/90* (2013.01); *C09K 11/06* (2013.01); *C09K 2211/1018* (2013.01); *H01L 51/0072* (2013.01); *H01L 51/5012* (2013.01); *C07D 401/10* (2013.01); *C07D 403/10* (2013.01); *C07D 487/04* (2013.01); *Y10S 428/917* (2013.01)

(58) Field of Classification Search
None
See application file for complete search history.

(56) References Cited

U.S. PATENT DOCUMENTS

| | | | |
|---|---|---|---|
| 2,675,380 | A | 4/1954 | Fielden et al. |
| 5,153,073 | A | 10/1992 | Ohnuma et al. |
| 5,952,115 | A * | 9/1999 | Hu et al. ....................... 428/690 |
| 6,951,693 | B2 | 10/2005 | Hosokawa et al. |
| 2007/0237984 | A1 | 10/2007 | Matsuura et al. |
| 2008/0122344 | A1 | 5/2008 | Shin et al. |
| 2008/0124455 | A1 | 5/2008 | Shin et al. |
| 2009/0017330 | A1 | 1/2009 | Iwakuma et al. |
| 2009/0096356 | A1 * | 4/2009 | Murase et al. ................. 313/504 |
| 2009/0230852 | A1 * | 9/2009 | Lee et al. ..................... 313/504 |
| 2009/0242876 | A1 | 10/2009 | Brunner et al. |
| 2009/0302752 | A1 | 12/2009 | Parham et al. |
| 2010/0032658 | A1 | 2/2010 | Lee et al. |
| 2011/0031485 | A1 | 2/2011 | Kwak et al. |
| 2011/0253944 | A1 | 10/2011 | Han et al. |
| 2011/0266533 | A1 * | 11/2011 | Buesing et al. .................. 257/40 |

FOREIGN PATENT DOCUMENTS

| | | |
|---|---|---|
| EP | 1375624 A1 | 1/2004 |
| EP | 1650208 A1 | 4/2006 |
| EP | 2145936 A2 | 1/2010 |
| EP | 2202283 A1 | 6/2010 |
| JP | 06-322361 | 11/1994 |
| JP | 06-322361 A | 11/1994 |
| JP | 2000156290 A | 6/2000 |
| JP | 2000-229974 A | 8/2000 |
| JP | 2001-011436 A | 1/2001 |
| JP | 2005-048004 | 2/2005 |
| JP | 2008-071863 | 3/2008 |
| JP | 2008-071863 A | 3/2008 |
| JP | 2008-078362 | 4/2008 |
| JP | 2008-078362 A | 4/2008 |
| JP | 2008-214306 | 9/2008 |
| JP | 2008-214306 A | 9/2008 |
| JP | 2010-59147 A | 3/2010 |
| JP | 2010-073987 A | 4/2010 |
| JP | 2010-087408 A | 4/2010 |
| JP | 2010087408 A * | 4/2010 |
| JP | 2011-37831 A | 2/2011 |
| KR | 10-2006-0051609 A | 5/2006 |
| KR | 10-2007-0067612 A | 6/2007 |
| KR | 10-2007-0091643 A | 9/2007 |
| KR | 10-2008-0025933 A | 3/2008 |
| KR | 10-2008-0047210 A | 5/2008 |
| KR | 10-2008-0084979 A | 9/2008 |
| KR | 901887 B1 * | 6/2009 |

(Continued)

OTHER PUBLICATIONS

Machine translation of JP2008-078362. Date of publication Apr. 3, 2008.*
Translation of WO2007-046246. Date of publication: Apr. 2007.*
Machine translation of JP2010-087408. Date of publication: Apr. 15, 2010.*
European Patent Office, Partial European Search Report corresponding to U.S. Appl. No. 12/853,224, dated Nov. 18, 2010, 6 pages.
Registration Determination Certificate issued by the Korean Intellectual Property Office dated Dec. 29, 2011, 5 pages.

(Continued)

*Primary Examiner* — Andrew K Bohaty
(74) *Attorney, Agent, or Firm* — Knobbe Martens Olson & Bear LLP

(57) ABSTRACT

A condensed-cyclic compound represented by Formula 1 and an organic light emitting diode including the same:

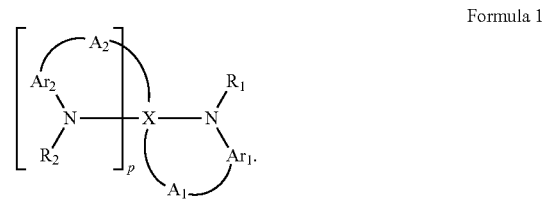

Formula 1

17 Claims, 1 Drawing Sheet

(56) References Cited

FOREIGN PATENT DOCUMENTS

| WO | WO 2007046246 A1 * | 4/2007 |
| WO | WO 2008/086851 A1 | 7/2008 |
| WO | WO 2009/008099 A1 | 1/2009 |
| WO | WO 2010/064871 A1 | 6/2010 |
| WO | WO 2010/074520 A2 | 7/2010 |
| WO | WO 2010083871 A1 * | 7/2010 |

OTHER PUBLICATIONS

Travis Thoms, Shinjiro Okada, Jian-Ping Chen, M. Furugori, Improved Host Material Design for Phosphorescent guest-Host Systems, Thin Solid Films, 2003, pp. 264-268, vol. 436, Canon Development Americas, Inc., San Jose, CA, www.sciencedirect.com.

Extended European Search Report issued by the European Patent Office dated Feb. 24, 2011, 19 pages.

Guoqiang Lin and Aimin Zhang, The First Synthesis of Optically Pure Biscarbazoles and Determination of Their Absolute Configurations, Tetrahedron Letters, 1999, pp. 341-344. vol. 40, Shanghai Institute of Organic Chemistry, Chinese Academy of Science, Shanghai, China.

Gennady M. Kosolapoff and Chester S. Schoepfle, Reaction of Phenylmagnesium Bromide and Diphenylmagnesium with 9,10—Diphenylacridyl Chloride and ρ-Dimethylaminotriphenylmethyl Chloride, Journal, Received Oct. 19, 1953, pp. 1276-1278, vol. 76, The Department of Chemistry, University of Michigan, Ann Arbor, Michigan.

Xue-Zhen Liu, Ze-Chang Liu, Zhi-Min Zong, Xian-Yong Wei, Jun Wang and Chul Well Lee, GC/MS Analysis of Water-Soluble Products from the Mild Oxidation of Longkou Brown Coal with H2O2; Journal, 2003, 1 p., vol. 17 (2), American Chemical Society.

N.P. Buu-Hoi, Odette Roussel and L. Petit, Carcinogenic nitrogen compounds. XXXV. Some heterocyclic derivatives of pyrene, Journal, 1963, 3 pages, Journal of the Chemical Society.

Seung Hwan Paek, Ki Seok Kim and Ksung Keun, Blue Organic Light Emitting Compound Having Excellent Thermal Stability and Organic Light Emitting Diode Comprising the Same, Patent, Repub. Korean Kongkae Taeho Kongbo.

Office Action issued by the Japanese Patent Office on Dec. 18, 2012 in the examination of Japanese Patent Application No. 2010-179608, 4 pages.

Maximilian Zander and Walter H. Franke, Synthese ciniger Naphthocarbazole, 1963, pp. 699-706, 96(3), J. Chem. Soc.

Maximilian Zander and Walter H. Franke, Synthesen von 9-Methyl-2.3; 6.7-dibenzo-carbazol, 9-Methyl-2.3;5.6-dibenzo-carbazol and Dinaphtho-[2'.3':2.3;2".3":5.6]-carbazol, 1965, pp. 2814-2821, 98(9), J. Chem. Soc.

Database Caplus [Online] Chemical Abstracts Service, Columbus, Ohio, US; 1970, Arient, Josef et al: "Anthraquinone dyes. VIII. Cyclization of simple dianthrimides with aluminum chloride in pyridine", XP002712558.

Database Caplus [Online] Chemical Abstracts Service, Columbus, Ohio, US; 1967, Zander, Maximilian et al: "Intramolecular rearrangements of annellated carbazoles", XP002712559.

Database Caplus [Online] Chemical Abstracts Service, Columbus, Ohio, US; 1965, Zander, Maximillian et al: "Syntheses of 9-methyl-2,3:6,7-dibenzocarbazole, 9-methyl-2,3: 5,6-dibenzocarbazole, and dinaphtho[2',3':2,3:2",3":5,6]carbazole", XP002712560.

Database Caplus [Online] Chemical Abstracts Service, Columbus, Ohio, US; 1965, Zander, Maximilian et al: "Relations between the ultraviolet spectra of multiple-ring carbazoles and aromatic hydrocarbons", XP002712561.

Database Caplus [Online] Chemical Abstracts Service, Columbus, Ohio, US; 1963, Zander, Maximilian et al: "Synthesis of several naphthocarbazoles", XP002712562.

Database Caplus [Online] Chemical Abstracts Service, Columbus, Ohio, US; 1927, "Heterocyclic compounds", XP002712563.

European Examination Report dated Jun. 13, 2014 issued in corresponding European Application No. 13179201.2.

Freeman et al. "Triphenylphosphine-Mediated Reductive Cyclization of 2-Nitrobiphenyls: A practical and Convenient Synthesis of Carbazoles" J. Org. Chem. 2005. pp. 5014-5019. V. 70, No. 13.

Miyaura et al. "Palladium-Catalyzed Cross-Coupling Reactions of Organoboron Compounds" Chem. Rev. 1995. pp. 2457-2483. V. 95, No. 7.

Song et al. "Construction of The Indole Nucleus through C—H Functionalization Reactions" ARKIVOC pp. 390-449. V. 2010, Part (i).

Suzuki. "Carbon—Carbon Bonding Made Easy" Chem. Commun. 2005. pp. 4759-4763.

Appeal Decision issued Mar. 3, 2015, in corresponding JP Application No. 2010-179608.

* cited by examiner

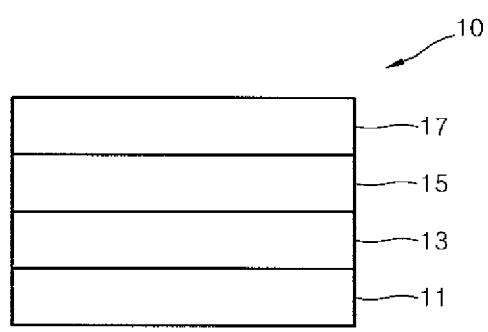

CONDENSED-CYCLIC COMPOUND AND ORGANIC LIGHT EMITTING DIODE HAVING ORGANIC LAYER INCLUDING THE SAME

CROSS-REFERENCE TO RELATED PATENT APPLICATION

This application claims the benefit of Korean Patent Application No. 10-2009-0073522, filed on Aug. 10, 2009, in the Korean Intellectual Property Office, the disclosure of which is incorporated herein in its entirety by reference.

BACKGROUND

1. Field

A condensed-cyclic compound and an organic light emitting diode having an organic layer including the condensed-cyclic are provided.

2. Description of the Related Art

Organic light emitting diodes are self-emission devices, have wide viewing angles, high contrast ratios, short response time, high luminosity, low driving voltages, high response rates, and produce various colors.

A conventional organic light emitting diode may have the following structure. An anode is formed on a substrate, and then a hole transport layer, a light emitting layer, an electron transport layer, and a cathode are sequentially formed on the anode. In this regard, each of the hole transport layer, the light emitting layer, and the electron transport layer is an organic thin film formed of an organic compound.

An organic light emitting diode having the structure described above may have the following driving principle.

When a voltage is applied between the anode and the cathode, holes injected from the anode move to the light emitting layer through the hole transport layer, and electrons injected from the cathode move to the light emitting layer through the electron transport layer. The holes and electrons, which are carriers, are recombined in the light emitting layer to form excitons. These excitons are changed from an excited state to a ground state, thereby generating light.

SUMMARY

The present embodiments provide a compound capable of providing an organic light emitting diode having a low driving voltage, a high current density, high efficiency, high quantum efficiency, and high luminosity.

According to an aspect of the present embodiments, there is provided a condensed-cyclic compound represented by Formula 1:

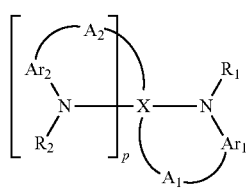

Formula 1 where X is selected from the group consisting of a substituted or unsubstituted $C_8$-$C_{30}$ aromatic polycyclic core and a substituted or unsubstituted $C_3$-$C_{30}$ heteroaromatic polycyclic core; $Ar_1$ and $Ar_2$ are, each independently, selected from the group consisting of a substituted or unsubstituted $C_6$-$C_{30}$ arylene group, and a substituted or unsubstituted $C_3$-$C_{30}$ heteroarylene group; $A_1$ and $A_2$ are, each independently, a divalent linking group represented by —[C($Q_1$)($Q_2$)]$_q$- where $Q_1$ and $Q_2$ are, each independently, selected from the group consisting of a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, and a substituted or unsubstituted $C_3$-$C_{30}$ heteroaryl group, and q is an integer from 0 to 3; $R_1$ and $R_2$ are, each independently, selected from the group consisting of a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, a substituted or unsubstituted $C_3$-$C_{30}$ heteroaryl group, and a group represented by —N($Q_3$)($Q_4$) where $Q_3$ and $Q_4$ are, each independently, selected from the group consisting of a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, and a substituted or unsubstituted $C_3$-$C_{30}$ heteroaryl group, and $Q_3$ and $Q_4$ are optionally fused with each other, or linked to each other by a single bond, a double bond, or a $C_1$-$C_3$ alkylene group, thereby forming a saturated or unsaturated ring; and p is an integer 0 to 10, wherein at least two groups selected from the group consisting of substituents of X, $Ar_1$, $Ar_2$, $R_1$, $R_2$, $Q_1$, and $Q_2$ are optionally fused with each other, or linked to each other by a single bond or a double bond, thereby forming a saturated or unsaturated ring.

According to another aspect of the present embodiments, there is provided an organic light emitting diode comprising: a first electrode, a second electrode facing the first electrode, and an organic layer interposed between the first electrode and the second electrode, wherein the organic layer comprises the condensed-cyclic compound of Formula 1.

BRIEF DESCRIPTION OF THE DRAWINGS

The above and other features and advantages of the present embodiments will become more apparent by describing in detail exemplary embodiments thereof with reference to FIG. 1 showing a schematic view of an organic light emitting diode according to an embodiment.

DETAILED DESCRIPTION

A condensed-cyclic compound according to an embodiment is represented by Formula 1:

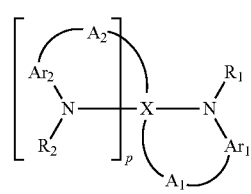

Formula 1 where X may be selected from the group consisting of a substituted or unsubstituted $C_8$-$C_{30}$ aromatic polycyclic core and a substituted or unsubstituted $C_3$-$C_{30}$ heteroaromatic polycyclic core. For example, X may be selected from the group consisting of a substituted or unsubstituted $C_8$-$C_{16}$ aromatic polycyclic core and a substituted or unsubstituted $C_3$-$C_{16}$ heteroaromatic polycyclic core.

In the present specification, the term "aromatic polycyclic core" refers to a polycyclic system in which at least two aromatic rings are fused with each other, or are linked to each other by a single bond. Also, in the present specification, the term "heteroaromatic polycyclic core" refers to a polycyclic system in which either at least two heteroaromatic rings, or at least one heteroaromatic ring and at least one aromatic ring are fused with each other, or are linked to each other by a single bond, wherein each of the heteroaromatic rings may include at least one hetero atom selected from the group consisting of N, O, P and S.

For example, in Formula 1, X may be selected from the group consisting of a substituted or unsubstituted pentalene core, a substituted or unsubstituted indene core, a substituted or unsubstituted naphthalene core, a substituted or unsubstituted azulene core, a substituted or unsubstituted heptalene core, a substituted or unsubstituted indacene core, a substituted or unsubstituted acenaphthylene core, a substituted or unsubstituted fluorene core, a substituted or unsubstituted phenalene core, a substituted or unsubstituted phenanthrene core, a substituted or unsubstituted anthracene core, a substituted or unsubstituted fluoranthene core, a substituted or unsubstituted triphenylene core, a substituted or unsubstituted pyrene core, a substituted or unsubstituted chrysene core, a substituted or unsubstituted naphthacene core, a substituted or unsubstituted picene core, a substituted or unsubstituted perylene core, a substituted or unsubstituted pentaphene core, a substituted or unsubstituted hexacene core, a substituted or unsubstituted pyrrole core, a substituted or unsubstituted pyrazole core, a substituted or unsubstituted imidazole core, a substituted or unsubstituted imidazoline core, a substituted or unsubstituted pyridine core, a substituted or unsubstituted pyrazine core, a substituted or unsubstituted pyrimidine core, a substituted or unsubstituted indole core, a substituted or unsubstituted purine core, a substituted or unsubstituted quinoline core, a substituted or unsubstituted phthalazine core, a substituted or unsubstituted indolizine core, a substituted or unsubstituted naphthyridine core, a substituted or unsubstituted quinazoline core, a substituted or unsubstituted cinnoline core, a substituted or unsubstituted indazole core, a substituted or unsubstituted carbazole core, a substituted or unsubstituted phenazine core, a substituted or unsubstituted phenanthridine core, a substituted or unsubstituted pyran core, a substituted or unsubstituted chromene core, a substituted or unsubstituted benzofuran core, a substituted or unsubstituted thiophene core, a substituted or unsubstituted benzothiophene core, a substituted or unsubstituted isothiazole core, a substituted or unsubstituted isoxazole core, and a substituted or unsubstituted phenyl-benzene core, but is not limited thereto.

For example, X may be selected from the group consisting of a substituted or unsubstituted anthracene core, a substituted or unsubstituted naphthalene core, a substituted or unsubstituted phenyl-benzene core, and a substituted or unsubstituted pyrene core, but is not limited thereto.

X may include at least one substituent or may be unsubstituted. If X includes at least one substituent, at least one substituent may be, each independently, selected from the group consisting of a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, a substituted or unsubstituted $C_3$-$C_{30}$ heteroaryl group, and a group represented by —N($Q_5$)($Q_6$), where $Q_5$ and $Q_6$ are, each independently, selected from the group consisting of a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, and a substituted or unsubstituted $C_3$-$C_{30}$ heteroaryl group. In this regard, $Q_5$ and $Q_6$ may be optionally fused with each other, or linked to each other by a single bond, a double bond, or a $C_1$-$C_3$ alkylene group, thereby forming a saturated or unsaturated ring.

For example, the at least one substituent may be, each independently, selected from the group consisting of a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, a substituted or unsubstituted $C_3$-$C_{16}$ heteroaryl group, and a group represented by —N($Q_5$)($Q_6$) where $Q_5$ and $Q_6$ are, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group, but is not limited thereto.

According to another embodiment, the at least one substituent may be, each independently, selected from the group consisting of a heavy hydrogen atom, a halogen atom, a hydroxyl group, a cyano group, a $C_6$-$C_{16}$ aryl group, and a group represented by —N($Q_5$)($Q_6$) where $Q_5$ and $Q_6$ may be, each independently, selected from the group consisting of a hydrogen atom, a heavy hydrogen atom, a halogen atom, a hydroxyl group, a cyano group, and a $C_6$-$C_{16}$ aryl group (e.g., a phenyl group, a naphthyl group, or an anthracenyl group). In this regard, $Q_5$ and $Q_6$ may be optionally fused with each other, or linked to each other by a single bond, or a $C_1$-$C_3$ alkylene group, thereby forming a saturated or unsaturated ring. For example, each of $Q_5$ and $Q_6$ may be a phenyl group, and these phenyl groups may be optionally linked by a single bond, thereby forming a carbazolyl ring.

For example, the at least one substituents may be a phenyl group, a halophenyl group, a $C_1$-$C_{10}$ alkylphenyl group, a $C_1$-$C_{10}$ alkoxyphenyl group, a naphthyl group, a halonaphthyl group, a $C_1$-$C_{10}$ alkylnaphthyl group, a $C_1$-$C_{10}$ alkoxynaphthyl group, an anthracenyl group, a haloanthracenyl group, a $C_1$-$C_{10}$ alkylanthracenyl group, a $C_1$-$C_{10}$ alkoxyanthracenyl group, a pyridinyl group, a halopyridinyl group, a $C_1$-$C_{10}$ alkylpyridinyl group, a $C_1$-$C_{10}$ alkoxypyridinyl group, or a group represented by —N($Q_5$)($Q_6$) where $Q_5$ and $Q_6$ are, each independently, selected from the group consisting of a phenyl group, a halophenyl group, a $C_1$-$C_{10}$ alkylphenyl group, a $C_1$-$C_{10}$ alkoxyphenyl group, a naphthyl group, a halonaphthyl group, a $C_1$-$C_{10}$ alkylnaphthyl group, a $C_1$-$C_{10}$ alkoxynaphthyl group, an anthracenyl group, a haloanthracenyl group, a $C_1$-$C_{10}$ alkylanthracenyl group, and a $C_1$-$C_{10}$ alkoxyanthracenyl group, and $Q_5$ and $Q_6$ are optionally linked to each other to form a saturated or unsaturated ring (e.g. $Q_5$ and $Q_6$ may be linked to each other, thereby forming a carbazolyl group together with but is not limited thereto.

In Formula 1, $Ar_1$ and $Ar_2$ may be, each independently, selected from the group consisting of a substituted or unsubstituted $C_6$-$C_{30}$ arylene group, and a substituted or unsubstituted $C_3$-$C_{30}$ heteroarylene group. For example, $Ar_1$ and $Ar_2$ may be, each independently, selected from the group consisting of a substituted or unsubstituted $C_6$-$C_{16}$ arylene group, and a substituted or unsubstituted $C_3$-$C_{16}$ heteroarylene group, but is not limited thereto.

For example, $Ar_1$ and $Ar_2$ may be, each independently, selected from the group consisting of a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted benzofuranylene group, a substituted or unsubstituted thiophenylene group, a substituted or unsubstituted benzothiophenylene group, a substituted or unsubstituted isothiazolylene group, and a substituted or unsubstituted isoxazolylene group, but is not limited thereto.

According to another embodiment, $Ar_1$ and $Ar_2$ may be, each independently, selected from the group consisting of a substituted or unsubstituted phenylene group, a substituted or unsubstituted naphthylene group, and a substituted or unsubstituted anthracenylene group, but is not limited thereto.

In Formula 1, $A_1$ and $A_2$ may be, each independently, selected from the group consisting of divalent linking group represented by —$[C(Q_1)(Q_2)]_q$-.

In the condensed-cyclic compound of Formula 1, at least one of the atoms in a ring and are included in X may be linked to at least one of the atoms that are included in $Ar_1$ and/or $Ar_2$ via $A_1$ and/or $A_2$, thereby forming a saturated ring or unsaturated ring and thus forming a backbone in Formula 1. In the condensed-cyclic compound of Formula 1, each of aryl amine moieties (for example, —$N(Ar_1)(R_1)$ and —$N(Ar_2)(R_2)$ in Formula 1), which may relatively lack electrical stability and/or thermal stability, forms a ring (for example, in Formula 1, $Ar_2$ and X form a ring by $A_2$ and/or $Ar_1$ and X form a ring by $A_1$), and thus dissolution of a C—N bond may be prevented and relatively excellent heat resistance and/or electrical stability are obtained. Thus, an organic light emitting diode employing the condensed-cyclic compound of Formula 1 has low driving voltage, high current density, high luminosity, high efficiency, and long lifetime.

$Q_1$ and $Q_2$ may be, each independently, selected from the group consisting of a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, and a substituted or unsubstituted $C_3$-$C_{30}$ heteroaryl group.

For example, $Q_1$ and $Q_2$ may be, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group.

According to another embodiment, $Q_1$ and $Q_2$ may be, each independently, selected from the group consisting of a hydrogen atom, a heavy hydrogen atom, a halogen atom, a $C_1$-$C_{10}$ alkyl group, a $C_1$-$C_{10}$ alkoxy group, and $C_6$-$C_{16}$ aryl group, but is not limited thereto.

For example, $Q_1$ and $Q_2$ may be, each independently, selected from the group consisting of a hydrogen atom, a methyl group, an ethyl group, a propyl group, a butyl group, a methoxy group, an ethoxy group, and a propoxy group, but is not limited thereto.

Also, q may be an integer 0 to 3. If q is 0 in Formula 1, at least one of the atoms that comprise a ring and are included in X may be linked to at least one of the atoms that are included in $Ar_1$ and/or $Ar_2$ via single bond, which will be described in detail later in another embodiment.

According to another embodiment, q may be 0. According to another embodiment, q may be an integer from 1 to 3.

In Formula 1, $R_1$ and $R_2$ may be, each independently, selected from the group consisting of a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, a substituted or unsubstituted $C_3$-$C_{30}$ heteroaryl group, and a group represented by —$N(Q_3)(Q_4)$ where $Q_3$ and $Q_4$ may be, each independently, selected from the group consisting of a hydrogen atom, a heavy hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, and a substituted or unsubstituted $C_3$-$C_{30}$ heteroaryl group. In this regard, $Q_3$ and $Q_4$ may be, optionally, fused with each other, or linked to each other by a single bond, a double bond, or a $C_1$-$C_3$ alkylene group, thereby forming a saturated ring or unsaturated ring.

For example, $R_1$ and $R_2$ may be, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, a substituted or unsubstituted $C_3$-$C_{16}$ heteroaryl group, and a group represented by —N($Q_3$)($Q_4$) where $Q_3$ and $Q_4$ may be, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group, but is not limited thereto. In this regard, $Q_3$ and $Q_4$ may be fused with each other, or linked to each other by a single bond, a double bond, or a $C_1$-$C_3$ alkylene group, thereby forming a saturated ring or unsaturated ring.

According to an embodiment, $R_1$ and $R_2$ may be, each independently, selected from the group consisting of a hydrogen atom, a heavy hydrogen atom, a halogen atom, a hydroxyl group, a cyano group, a $C_1$-$C_{10}$ alkyl group, a $C_1$-$C_{10}$ alkoxy group, and a $C_6$-$C_{16}$ aryl group, but is not limited thereto.

For example, $R_1$ and $R_2$ may be, each independently, a methyl group, an ethyl group, a propyl group, a methoxy group, an ethoxy group, a propoxy group, a phenyl group, a halophenyl group, a $C_1$-$C_{10}$ alkylphenyl group, a $C_1$-$C_{10}$ alkoxyphenyl group, a naphthyl group, a halonaphthyl group, a $C_1$-$C_{10}$ alkylnaphthyl group, a $C_1$-$C_{10}$ alkoxynaphthyl group, an anthracenyl group, a haloanthracenyl group, a $C_1$-$C_{10}$ alkylanthracenyl group, a $C_1$-$C_{10}$ alkoxyanthracenyl group, a pyridinyl group, halopyridinyl group, a $C_1$-$C_{10}$ alkylpyridinyl group, a $C_1$-$C_{10}$ alkoxypyridinyl group, or a group represented by —N($Q_3$)($Q_4$) where $Q_3$ and $Q_4$ may be, each independently, selected from the group consisting of a phenyl group, a halophenyl group, a $C_1$-$C_{10}$ alkylphenyl group, a $C_1$-$C_{10}$ alkoxyphenyl group, a naphthyl group, a halonaphthyl group, a $C_1$-$C_{10}$ alkylnaphthyl group, a $C_1$-$C_{10}$ alkoxynaphthyl group, anthracenyl group, haloanthracenyl group, a $C_1$-$C_{10}$ alkylanthracenyl group, and a $C_1$-$C_{10}$ alkoxyanthracenyl group, and $Q_3$ and $Q_4$ may be, optionally, linked to each other to form a saturated or unsaturated ring (for example, $Q_3$ and $Q_4$ may be linked to each other to form a carbazolyl group together with —N), but is not limited thereto.

In Formula 1, p may be an integer from 0 to 10. For example, p may be 0, 1, 2, or 3, but is not limited thereto, and may be selected from this range described above in consideration of the structure of X.

Among $Ar_1$, $Ar_2$, $R_1$, $R_2$, $Q_1$, $Q_2$ and the substituents of X which have been described above, at least two groups may be, optionally, fused with each other, or linked to each other by a single bond or a double bond, thereby forming a saturated ring or unsaturated ring.

According to an embodiment, among atoms that comprise the backbone of X in Formula 1, an element connected to $A_1$ and an element connected N may be connected to each other by a single bond or a double bond. In addition, among the atoms that comprise the backbone of X in Formula 1, an element connected to $A_2$ and an element connected to N may be connected to each other by a single bond or a double bond.

According to another embodiment, the condensed-cyclic compound may be represented by any one of Formulas 1a-1 to 1h-1 (X is a substituted or unsubstituted anthracene core, a substituted or unsubstituted naphthalene core, a substituted or unsubstituted phenyl-benzene core, or a substituted or unsubstituted pyrene core, and q is 0), but may also be represented by other formulas:

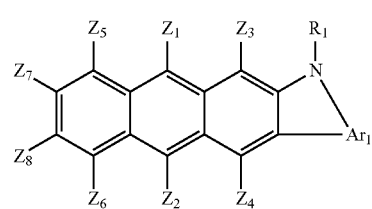

Formula 1a-1

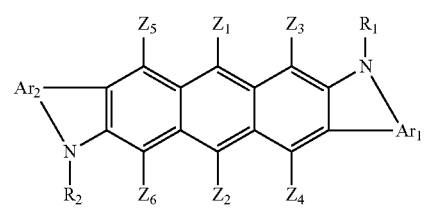

Formula 1b-1

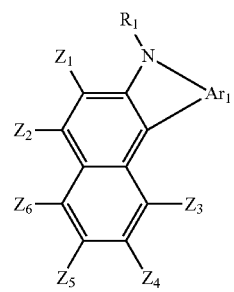

Formula 1c-1

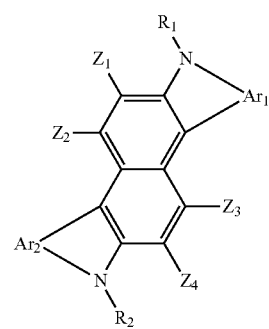

Formula 1d-1

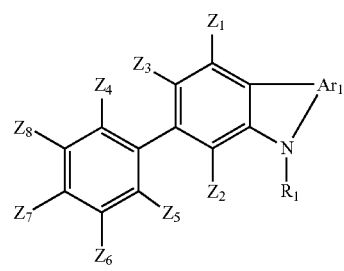

Formula 1e-1

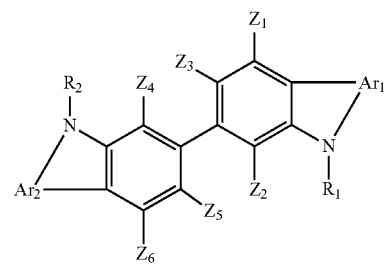

Formula 1f-1

Formula 1g-1
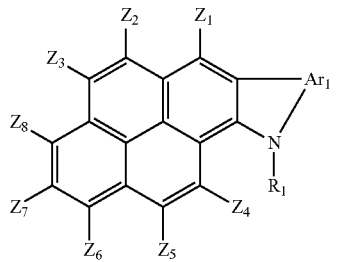

Formula 1h-1
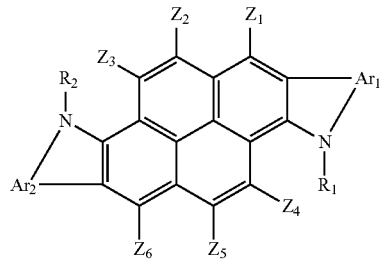

According to another embodiment, the condensed-cyclic compound may be represented by any one of Formulas 1a-2 to 1h-2 (X is a substituted or unsubstituted anthracene core, a substituted or unsubstituted naphthalene core, a substituted or unsubstituted phenyl-benzene core, or a substituted or unsubstituted pyrene core, and q is not 0), but may also be represented by other formulas:

Formula 1a-2
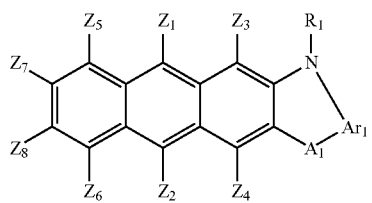

Formula 1b-2
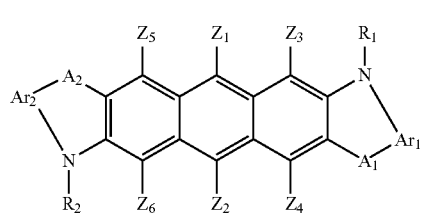

Formula 1c-2
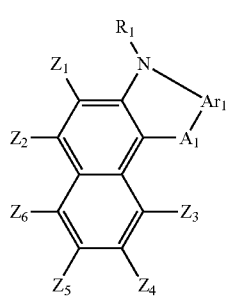

Formula 1d-2
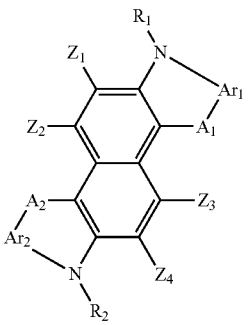

Formula 1e-2
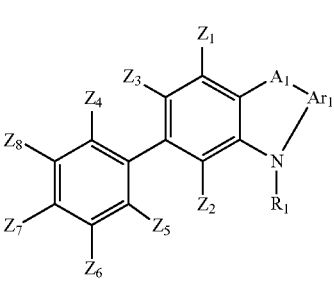

Formula 1f-2
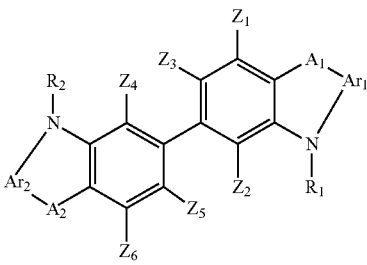

Formula 1g-2

Formula 1h-2

According to another embodiment, the condensed-cyclic compound may be represented by any one of Formulas 2a-1 to 2h-1 (X is a substituted or unsubstituted anthracene core, a substituted or unsubstituted naphthalene core, a substituted or unsubstituted phenyl-benzene core, or a substituted or unsubstituted pyrene core, q is 0, and $Ar_1$ and $Ar_2$ are substituted or unsubstituted phenylene groups), but may also be represented by other formulas:

Formula 2a-1
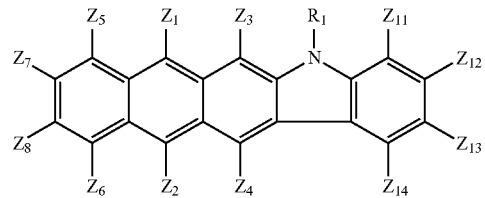

Formula 2b-1
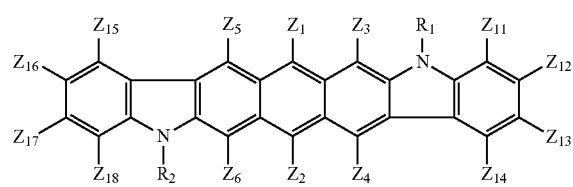

Formula 2c-1
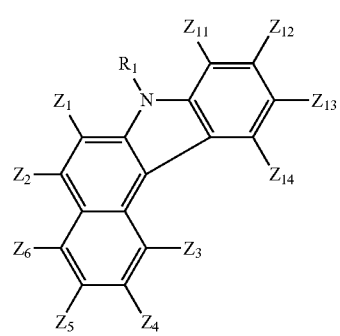

Formula 2d-1
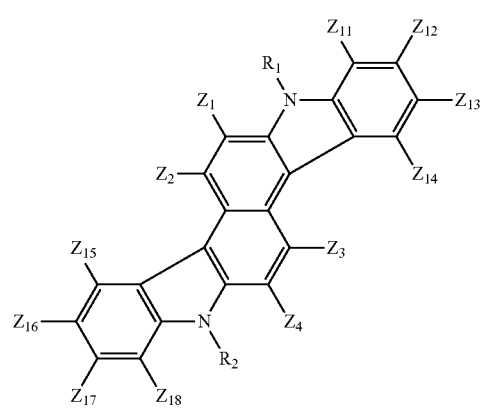

Formula 2e-1
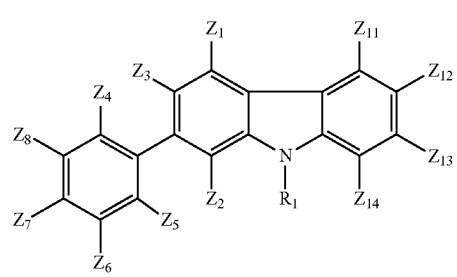

Formula 2f-1
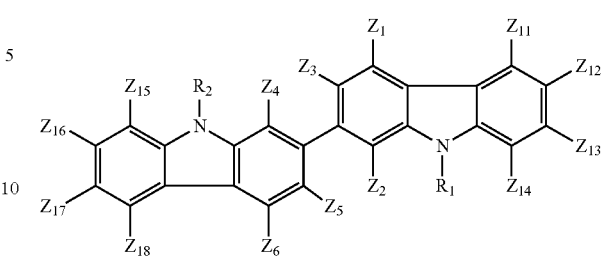

Formula 2g-1
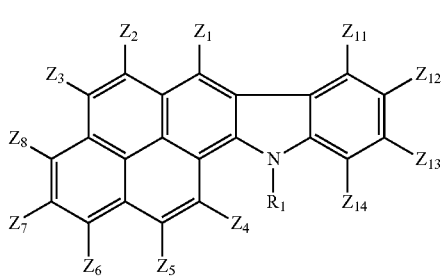

Formula 2h-1

According to another embodiment, the condensed-cyclic compound may be represented by any one of Formulas 2a-2 to 2h-2 (X is a substituted or unsubstituted anthracene core, a substituted or unsubstituted naphthalene core, a substituted or unsubstituted phenyl-benzene core, or a substituted or unsubstituted pyrene core, q is not 0, and $Ar_1$ and $Ar_2$ are substituted or unsubstituted phenylene groups), but may also be represented by other formulas:

Formula 2a-2
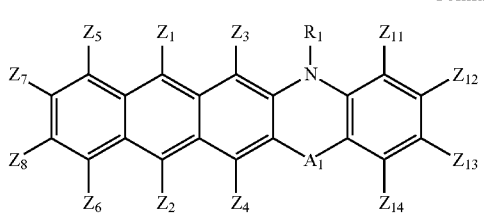

Formula 2b-2
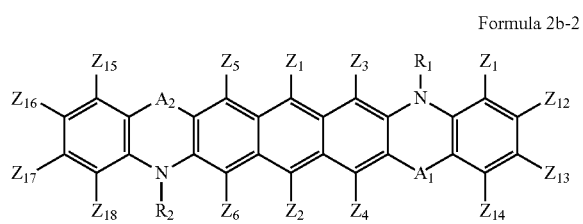

-continued
Formula 2c-2
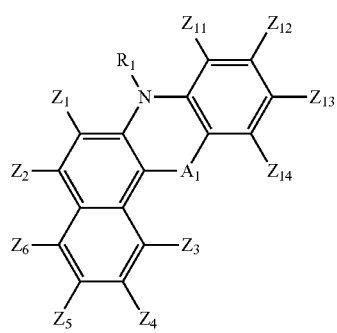
Formula 2d-2
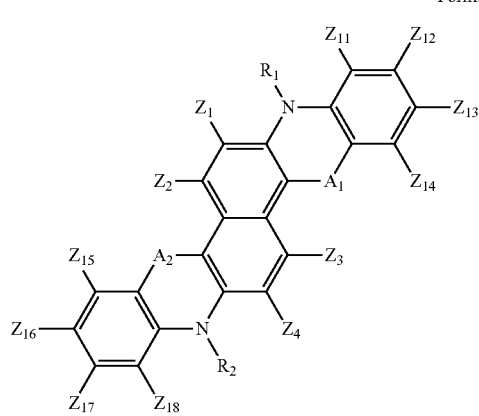
Formula 2e-2
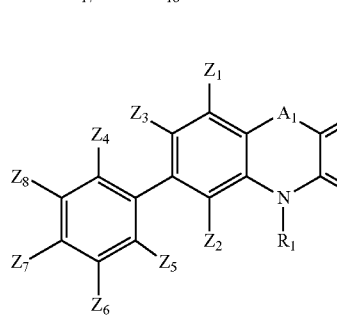
Formula 2f-2
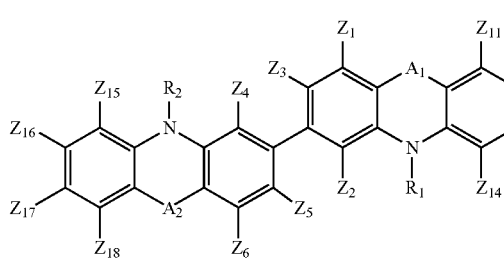
Formula 2g-2
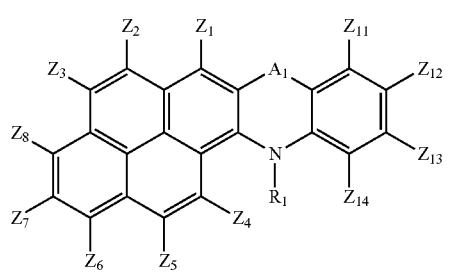
-continued
Formula 2h-2
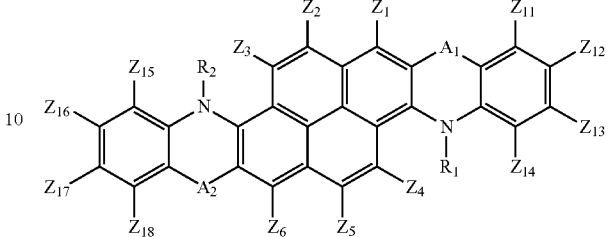
According to another embodiment, the condensed-cyclic compound may be represented by any one of Formulas 3a-1, 3a-2, 3c-1, 3c-2, 3e-1, 3e-2, 3g-1, and 3g-2, but may also be represented by other formulas:
Formula 3a-1
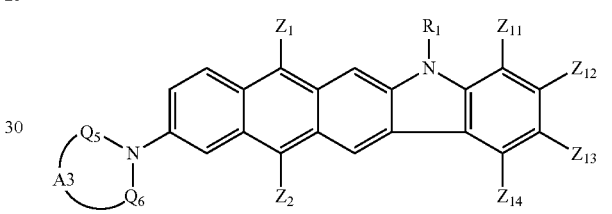
Formula 3a-2
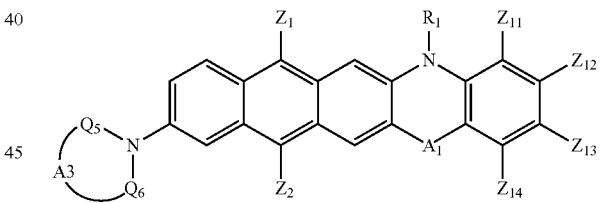
Formula 3c-1
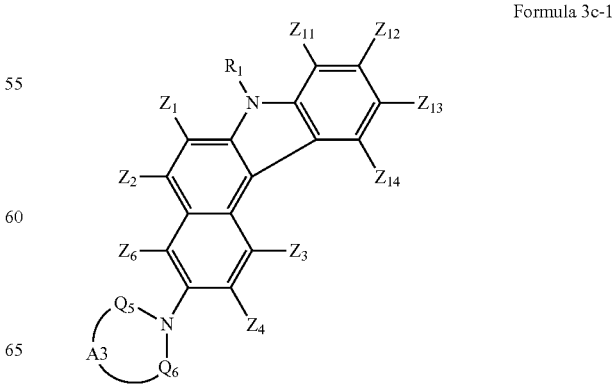

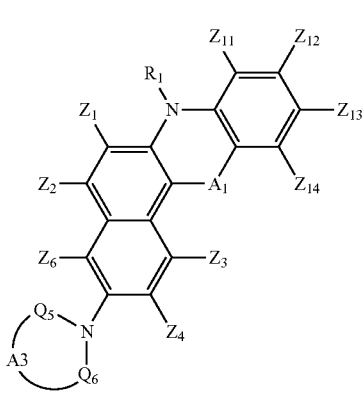

Formula 3c-2

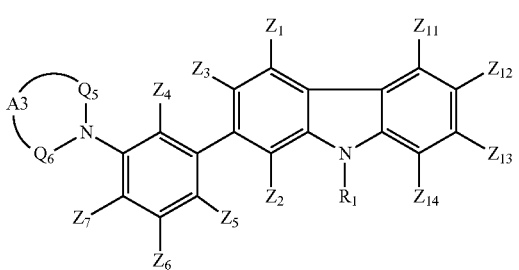

Formula 3e-1

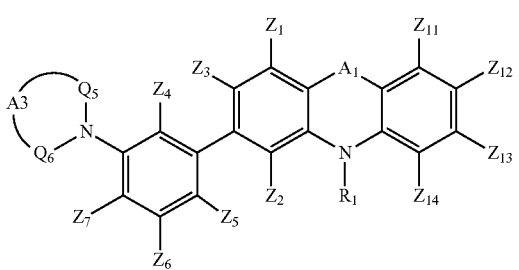

Formula 3e-2

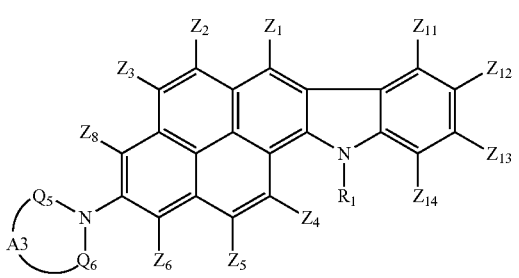

Formula 3g-1

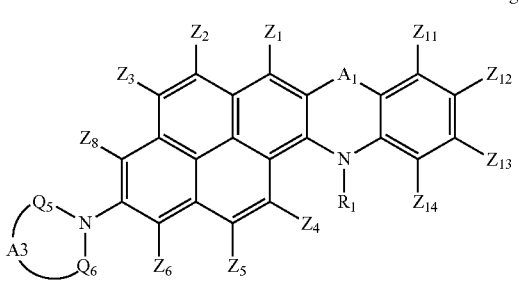

Formula 3g-2

With regard to Formulas 3a-1, 3a-2, 3c-1, 3c-2, 3e-1, 3e-2, 3g-1, and 3g-2, $A_3$ represents a single bond or a $C_1$-$C_3$ alkylene group.

For example, in Formulas 1a-1 to 3g-2, $Ar_1$ and $Ar_2$ may be, each independently, selected from the group consisting of a substituted or unsubstituted $C_6$-$C_{16}$ arylene group and a substituted or unsubstituted $C_3$-$C_{16}$ heteroarylene group (for example, a substituted or unsubstituted phenylene group, a substituted or unsubstituted naphthylene group, or a substituted or unsubstituted anthracenylene group); $A_1$ and $A_2$ may be, each independently, selected from the group consisting of divalent linking group represented by $-[C(Q_1)(Q_2)]_q$- where $Q_1$ and $Q_2$ may be, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group, and q may be an integer from 1 to 3; $R_1$ and $R_2$ may be, each independently, selected from the group consisting of a hydrogen atom, a heavy hydrogen atom, a halogen atom, a hydroxyl group, a cyano group, a substituted or unsubstituted $C_1$-$C_{10}$ alkyl group (for example, a methyl group, an ethyl group, a propyl group, or a butyl group), a substituted or unsubstituted $C_1$-$C_{10}$ alkoxy group, a substituted or unsubstituted $C_6$-$C_{16}$ aryl group (for example, a phenyl group, a naphthyl group, or an anthracenyl group), a substituted or unsubstituted $C_3$-$C_{16}$ heteroaryl group, and a group represented by $-N(Q_3)(Q_4)$ where $Q_3$ and $Q_4$ may be, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group, and $Q_3$ and $Q_4$ may be fused with each other, or linked to each other by a single bond, a double bond, or a $C_1$-$C_3$ alkylene group, thereby forming a saturated or unsaturated ring; and $Z_1$ to $Z_8$ and $Z_{11}$ to $Z_{18}$ may be, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group (for example, a phenyl group, a naphthyl group, or an anthracenyl group), a substituted or unsubstituted $C_3$-$C_{16}$ heteroaryl group, and a group represented by $-N(Q_5)(Q_6)$ where $Q_5$ and $Q_6$ may be, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group, and $Q_5$ and $Q_6$ may be optionally fused with each other, or linked to each other by a single bond, a double bond, or a $C_1$-$C_3$ alkylene group, thereby forming a saturated or unsaturated ring, but is not limited thereto.

According to another embodiment, the condensed-cyclic compound may be any one of Compounds 1 to 16 below, but is not limited thereto:

Compound 1
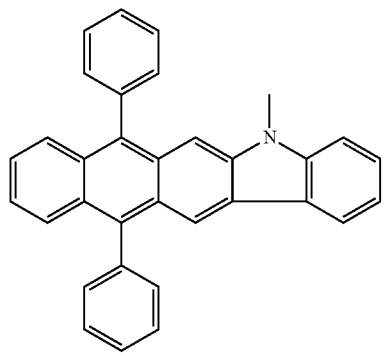
Compound 2
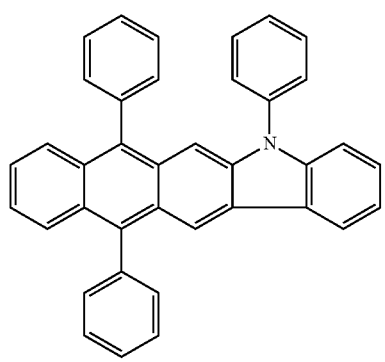
Compound 3
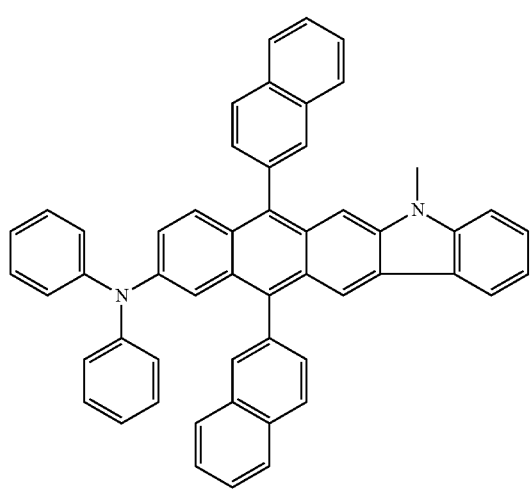
Compound 4
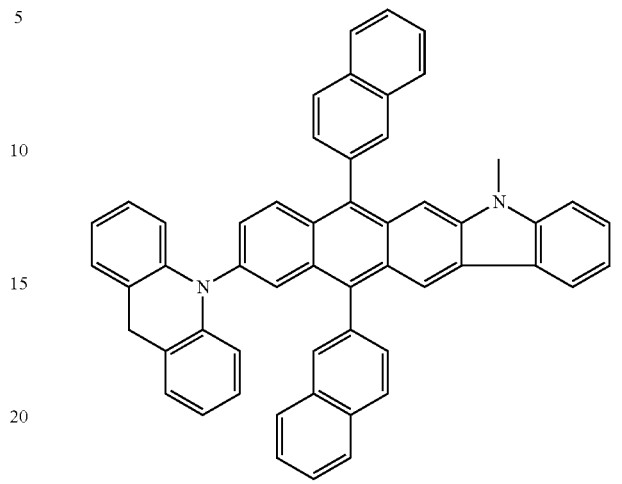
Compound 5
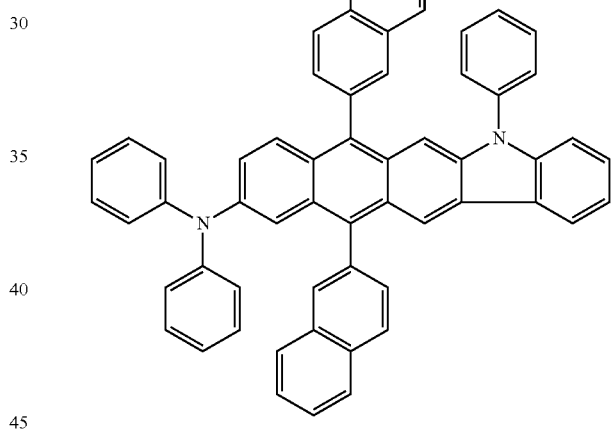
Compound 6
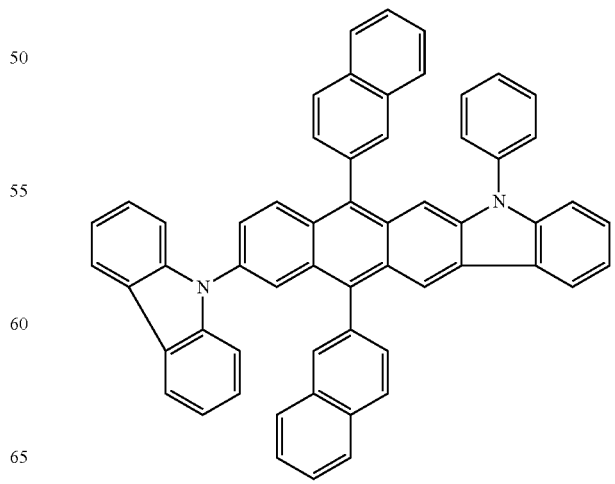

Compound 7
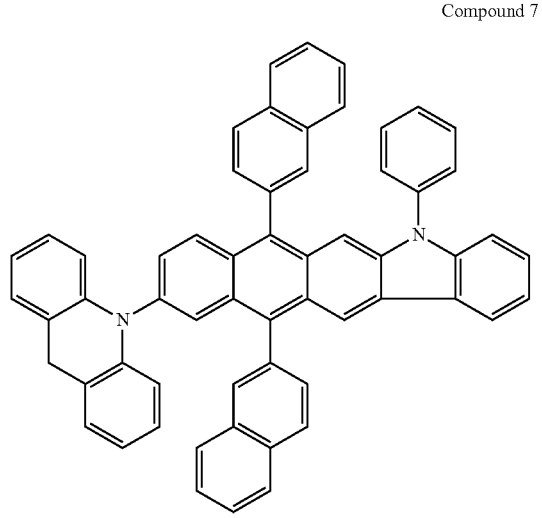
Compound 8
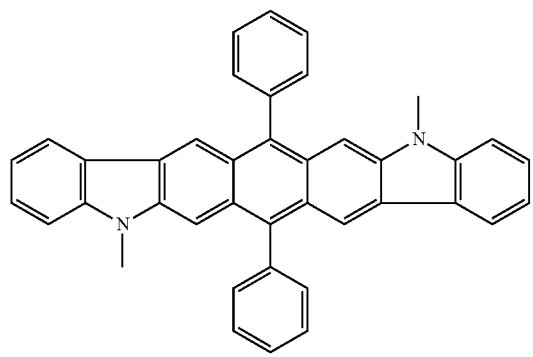
Compound 9
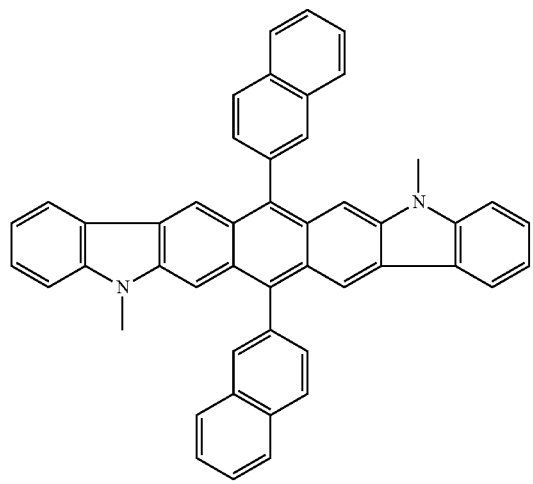
Compound 10
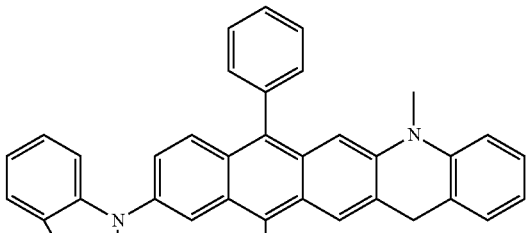
Compound 11
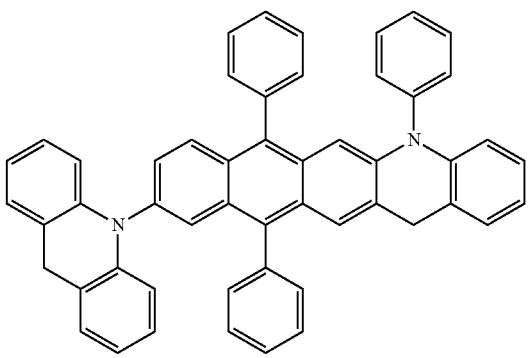
Compound 12
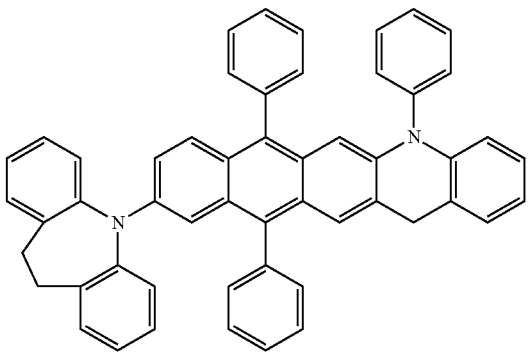
Compound 13
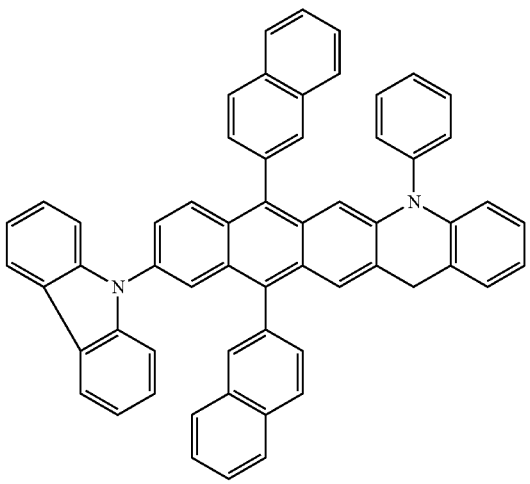

-continued

Compound 14

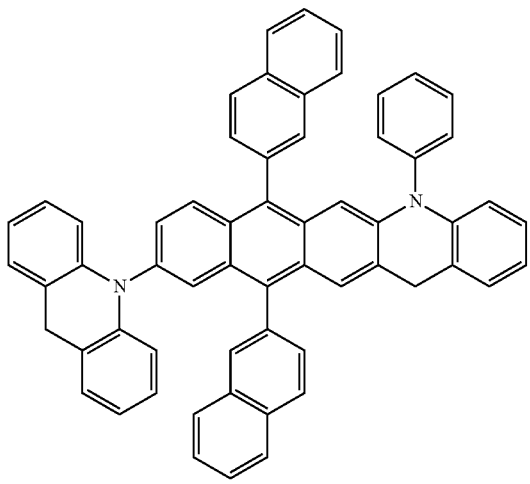

Compound 15

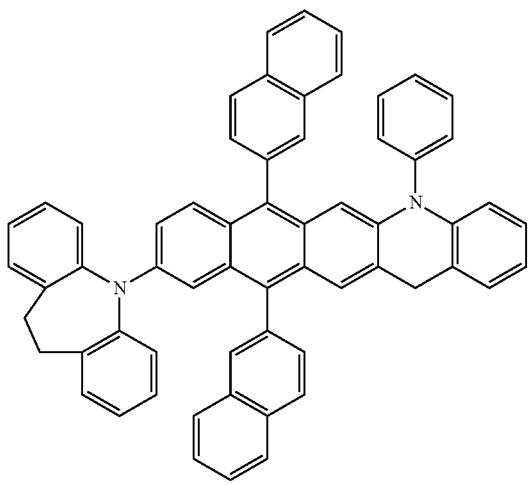

Compound 16

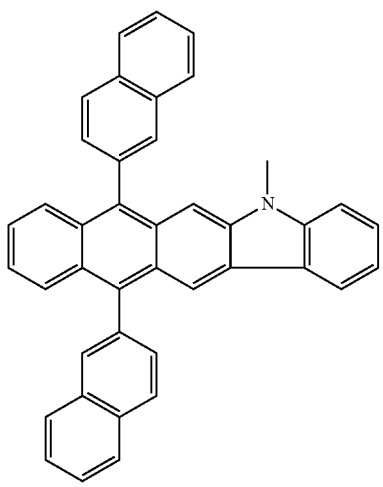

In the present specification, examples of the unsubstituted $C_1$-$C_{30}$ alkyl group include methyl, ethyl, propyl, isobutyl, sec-butyl, pentyl, iso-amyl, and hexyl, and at least one hydrogen atom in the alkyl group may be substituted with a halogen atom, a hydroxyl group, a nitro group, a cyano group, an amino group, an amidino group, a hydrazine group, a hydrazone group, a carboxylic group or a salt thereof, a sulfonic acid group or a salt thereof, a phosphoric acid group or a salt thereof, a $C_1$-$C_{30}$ alkyl group, a $C_1$-$C_{30}$ alkenyl group, a $C_1$-$C_{30}$ alkynyl group, a $C_6$-$C_{30}$ aryl group, or a $C_2$-$C_{20}$ heteroaryl group.

In the present specification, examples of the unsubstituted $C_1$-$C_{30}$ alkoxy group include —OA where A is the $C_1$-$C_{30}$ alkyl group described above such as methoxy, ethoxy, or isopropyloxy for example. In these alkoxy groups, at least one hydrogen atom may be substituted with the substituents which are used to substitute the alkyl group.

In the present specification, the unsubstituted $C_2$-$C_{30}$ alkenyl group refers to a system in which a carbon double bond is present in the middle or end of the alkyl group described above. Examples of the unsubstituted $C_2$-$C_{30}$ alkenyl group include ethenyl, propenyl, and butenyl. At least one hydrogen atoms in these alkenyl groups may be substituted with the substituents which are used to substitute the alkyl group.

In the present specification, the unsubstituted $C_2$-$C_{30}$ alkynyl group refers to a system in which a carbon triple bond is present in the middle or end of the alkyl group described above. Examples of the unsubstituted $C_2$-$C_{30}$ alkynyl group include acetylene, propylene, isopropylacetylene, t-butylacetylene. At least one hydrogen atoms in these alkynyl groups may be substituted with the substituents which are used to substitute the alkyl group.

In the present specification, the unsubstituted $C_6$-$C_{30}$ aryl group refers to a monovalent group having a carbocyclic aromatic system having at least one aromatic ring and 5-30 carbon atoms, and the unsubstituted $C_6$-$C_{30}$ arylene group refers to a divalent group having a carbocyclic aromatic system having at least one aromatic ring and 5-30 carbon atoms. If the aryl group and the arylene group include at least two rings, the at least two rings may be fused with each other, or linked to each other by a single bond. In the aryl group and the arylene group, at least one hydrogen atom may be substituted with the substituents which are used to substitute the alkyl group.

Examples of the substituted or unsubstituted $C_6$-$C_{30}$ aryl group include a phenyl group, a $C_1$-$C_{10}$ alkylphenyl group (for example, ethylphenyl group), a $C_1$-$C_{10}$ alkylbiphenyl group (for example, ethylbiphenyl group), a halophenyl group (for example, o-, m- and p-fluorophenyl groups, or a dichlorophenyl group), a dicyanophenyl group, a trifluoromethoxyphenyl group, o-, m-, and p-tolyl groups, o-, m- and p-cumenyl groups, a mesityl, phenoxyphenyl group, a (α,α-dimethylbenzene) phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthrenyl group, a triphenylenyle group, a pyrenyl group, a chrysenyl group, an ethylchrysenyl group, a picenyl group, a perylenyl group, a chloro perylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group. Examples of the substituted or unsubstituted $C_6$-$C_{30}$ arylene group may refer to the examples of the substituted or unsubstituted $C_6$-$C_{30}$ aryl group described above.

In the present specification, the unsubstituted $C_2$-$C_{30}$ heteroaryl group refers to a monovalent group having a system in which at least one aromatic ring has at least one hetero atom selected from N, O, P or S and the remaining ring atoms all are carbon atoms, and the unsubstituted $C_2$-$C_{30}$ heteroarylene group refers to a divalent group having a system which includes at least one aromatic ring having at least one hetero atom selected from N, O, P or S and the remaining ring atoms all are carbon atoms. In this regard, if the heteroaryl group and the heteroarylene group include at least two rings, the rings may be fused with each other, or linked to each other by a single bond. In the heteroaryl group and the heteroarylene group, at least one hydrogen atom may be substituted with the substituents which are used to substitute the alkyl group.

Examples of the unsubstituted $C_2$-$C_{30}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, and an isoquinolinyl group. Examples of the unsubstituted $C_2$-$C_{30}$ heteroarylene group may refer to the examples of the substituted or unsubstituted $C_6$-$C_{30}$ arylene group described above.

The condensed-cyclic compound represented by Formula 1 may be synthesized using a known organic synthesis method. A method of synthesizing the condensed-cyclic compound may be obvious to one of ordinary skill in the art by referring to the following embodiments.

For example, when p is 0, the condensed-cyclic compound of Formula 1 may be synthesized according to Reaction Scheme 1 below, but the synthesis method is not limited thereto:

Reaction Scheme 1

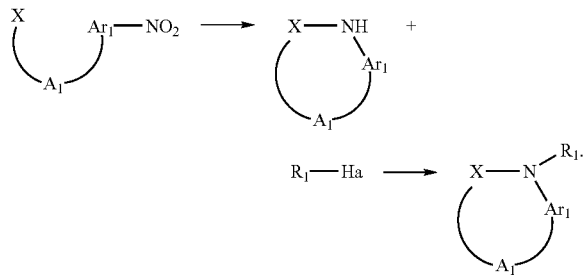

When p is, for example, 1, the condensed-cyclic compound of Formula 1 may be synthesized according to Reaction Scheme 2 below, but the synthesis method is not limited thereto is not limited thereto:

Reaction Scheme 2

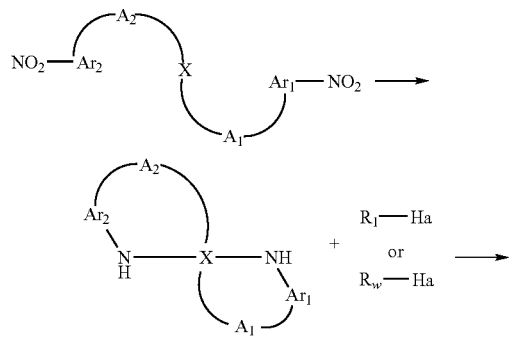

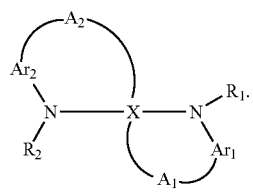

With regard to Reaction Schemes 1 and 2, Ha represents a halogen element (for example, —F, —Cl, —Br or —I).

The condensed-cyclic compound of Formula 1 may be included in an organic layer of an organic light emitting diode. Thus, an organic light emitting diode including a first electrode, a second electrode facing the first electrode, and an organic layer interposed between the first electrode and the second electrode, wherein the organic layer includes the condensed-cyclic compound of Formula 1, is provided.

The organic layer may be a light emitting layer or a hole transport layer, but is not limited thereto.

For example, when the organic layer is the light emitting layer, the light emitting layer may further include, in addition to the condensed-cyclic compound represented by Formula 1, a known host. However, the organic layer may also include other materials in another embodiment.

FIG. 1 is a schematic view of an organic light emitting diode 10 according to an embodiment. Hereinafter, the structure of the organic light emitting diode 10 and a method of manufacturing the organic light emitting diode 10 will be described.

The organic light emitting diode 10 includes a substrate 11, a first electrode 13, an organic layer 15, and a second electrode 17 sequentially formed in this stated order.

The substrate 11 may be any substrate that is used in a commonly used organic light emitting diode. For example, the substrate 11 may be a glass substrate or a transparent plastic substrate, either of which has high mechanical strength, high thermal stability, high transparency, surface smoothness and is waterproof.

The first electrode 13 may be formed by depositing or sputtering a first electrode material on the substrate 11. If the first electrode 13 is an anode, the first electrode material may include a material having a high work function constant so that holes are easily injected. The first electrode 13 may be a reflective electrode or a transmissive electrode. The first electrode material may be a material that is transparent and highly conductive, such as indium tin oxide (ITO), indium zinc oxide (IZO), tin oxide ($SnO_2$), or zinc oxide (ZnO). Alternatively, the first electrode material may be magnesium (Mg), aluminum (Al), aluminum-lithium (Al—Li), potassium (K), magnesium-indium (Mg—In), or magnesium-silver (Mg—Ag).

The organic layer 15 is formed on the first electrode 13. In the present specification, the term "organic layer" indicates the layers interposed between the first electrode 13 and the second electrode 17. For example, the organic layer may also include a metallic complex. For example, the organic layer may further include other materials other than an organic material.

The organic layer 15 may include at least one layer selected from the group consisting of a hole injection layer, a hole transport layer, a light emitting layer, a hole blocking layer, an electron transport layer, and an electron injection layer.

The hole injection layer (HIL) may be formed on the first electrode 13 using a method selected from various known methods such as a vacuum deposition method, a spin coating method, a cast method, or a Langmuir Blodgett (LB) method.

If the HIL is formed using a vacuum deposition method, deposition conditions may differ according to a compound selected for preparing a target layer, a target layer structure, and thermal characteristics, and for example, a deposition temperature may be from about 100 to about 500° C., a degree of vacuum may be from about $10^{-10}$ to about $10^{-3}$ torr, and a deposition speed may be from about 0.01 to about 100 Å/sec, but the deposition temperature, the degree of vacuum, and the deposition speed is not limited thereto.

If the HIL is formed using a spin coating method, coating conditions may differ according to a compound selected for preparing a target layer, a target layer structure, and thermal characteristics, and for example, a coating speed may be from about 2000 rpm to about 5000 rpm and a temperature at which a solvent used is removed after coating may be from about 80° C. to about 200° C., but the coating speed and the solvent removal temperature are not limited thereto.

A HIL material may be any known hole injection material and may be, for example, N,N'-diphenyl-N,N'-bis-[4-(phenyl-m-tolyl-amino)-phenyl]-biphenyl-4,4'-diamine (DNTPD) or a phthalocyanine compound such as a copper phthalocyanine, 4,4',4''-tris(3-methylphenylphenylamino)triphenylamine (m-MTDATA), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), or (polyaniline)/poly(4-styrenesulfonate) (PANI/PSS), but is not limited thereto. Exemplary compounds are shown below:

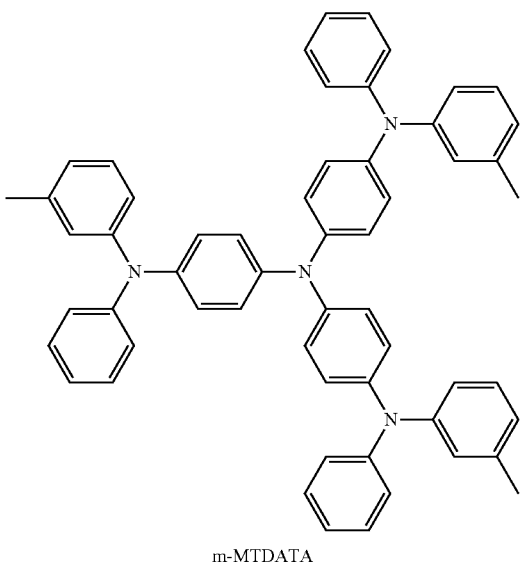

m-MTDATA

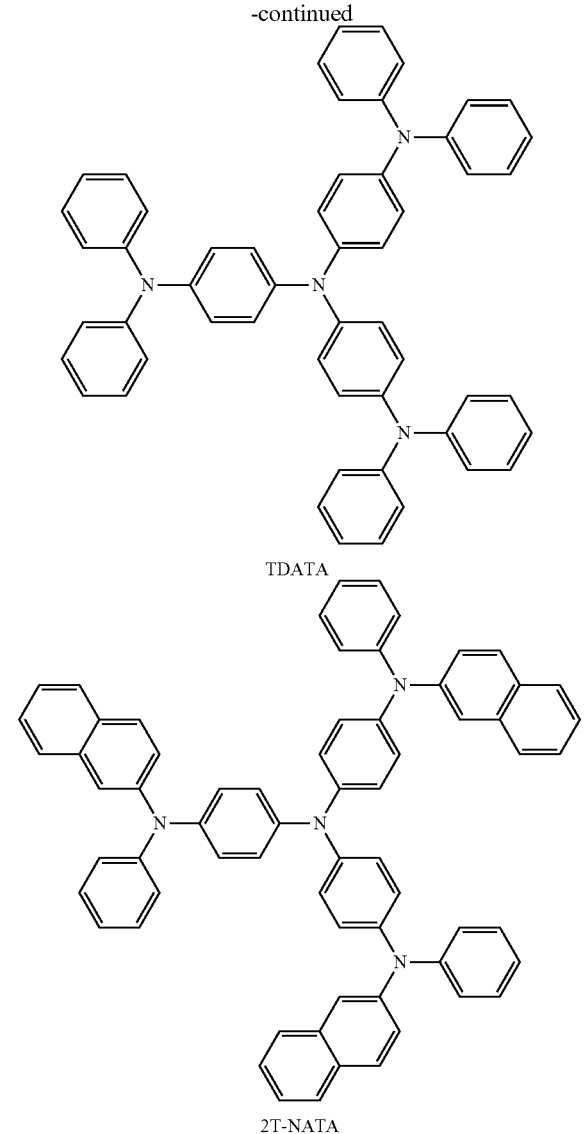

TDATA

2T-NATA

The thickness of the HIL may be from about 100 Å to about 10000 Å, for example, from about 100 Å to about 1000 Å. If the thickness of the HIL is within this range, satisfactory hole injection characteristics may be obtained without a substantial increase in the driving voltage of the organic light emitting diode.

The hole transport layer (HTL) may be formed on the HIL using a method selected from various known methods such as a vacuum deposition method, a spin coating method, a cast method, or an LB method. When the HTL is formed using a vacuum deposition method or a spin coating method, deposition conditions and coating conditions may differ according to a compound selected for preparing a target layer, but may be similar to those described with reference to the HIL.

A HTL material may be any known hole transport material, and may be, for example, a carbazole derivative such as N-phenylcarbazole or polyvinylcarbazole; an amine derivative having an aromatic condensation ring (such as N,N'-bis(3-methylphenyl)-N,N'-diphenyl-[1,1-biphenyl]-4,4'-diamine (TPD) or N,N'-di(naphthalene-1-yl)-N,N'-diphenyl benzidine (NPD); or a triphenylamine-based material, such as 4,4',4''-tris(N-carbazolyl)triphenylamine (TCTA). Among these HTL materials, TCTA may have, in addition to a hole transporting capability, a capability of blocking diffusion of excitons generated in the light emitting layer. Exemplary compounds are shown below:

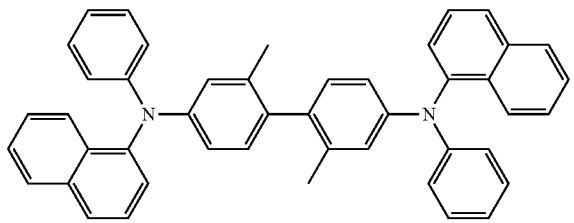

α-NPD

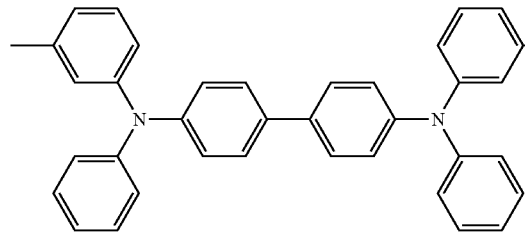

TPD

The thickness of the HTL may be from about 50 Å to about 1000 Å, for example, from about 100 Å to about 800 Å. If the thickness of the HTL is within this range, satisfactory hole transporting characteristics may be obtained without a substantial increase in the driving voltage of the organic light emitting diode.

The light emitting layer (EML) may be formed on the HTL using a method selected from various known methods such as a vacuum deposition method, a spin coating method, a cast method, or a LB method. When the EML is formed using a vacuum deposition method or a spin coating method, deposition conditions and coating conditions may differ according to a compound selected for preparing a target layer, but may be similar to those described with reference to the HIL.

The EML may include the condensed-cyclic compound of Formula 1 described above. The EML may include only the condensed-cyclic compound, or further include, in addition to the condensed-cyclic compound, a known host. The known host may be Alq$_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, or distyrylarylene (DSA), but is not limited thereto. Exemplary compounds are shown below:

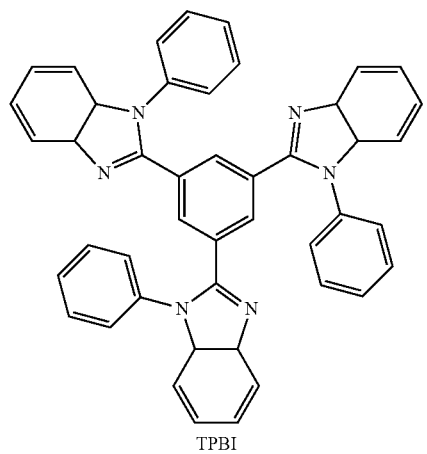

TPBI

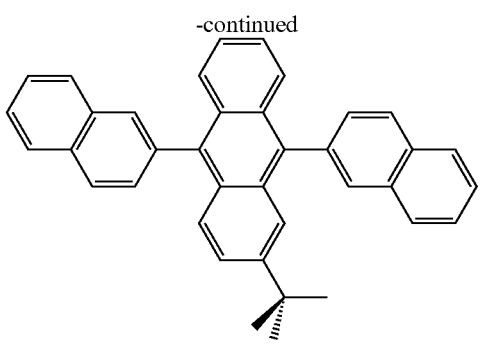

TBADN

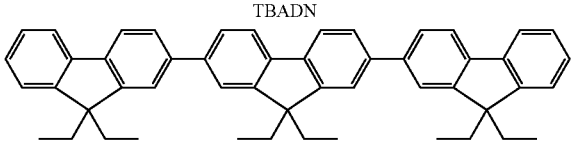

E3

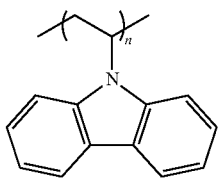

PVK

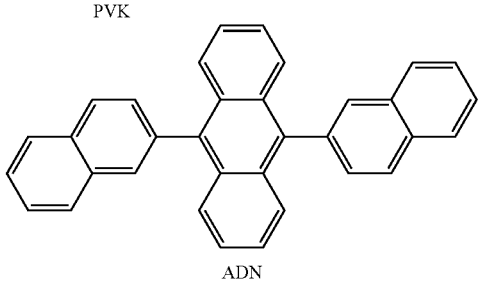

ADN

When the condensed-cyclic compound of Formula 1 (dopant) is used together with a host, the doping concentration of the condensed-cyclic compound may vary. For example, in general, the doping concentration of the condensed-cyclic compound may be from about 0.01 to about 15 parts by weight based on about 100 parts by weight of the host, but is not limited thereto.

The thickness of the EML may be from about 100 Å to about 1000 Å, for example, from about 200 Å to about 600 Å. If the thickness of the EML is within this range, excellent light emitting characteristics may be obtained without a substantial increase in the driving voltage of the organic light emitting diode.

When a phosphorescent dopant is used to form the EML, a hole blocking layer (HBL) may be further formed between the HTL and the EML. The HBL blocks triplet excitons or holes from diffusing into, for example, the ETL. When the HBL is formed using a vacuum deposition method or a spin coating method, deposition conditions and coating conditions may differ according to a compound selected for preparing a target layer, but may be similar to those described with reference to the HIL. A hole blocking material may be any known hole blocking material. For example, the hole blocking material may be an oxadiazole derivative, a triazole derivative, or a phenanthroline derivative.

The thickness of the HBL may be from about 50 Å to about 1000 Å, for example, from about 100 Å to about 300 Å. If the thickness of the HBL is within this range, excellent hole blocking characteristics may be obtained without a substantial increase in the driving voltage of the organic light emitting diode.

Then, electron transport layer (ETL) may be formed using a method selected from various known methods such as a vacuum deposition method, a spin coating method, or a cast method. When the ETL is formed using a vacuum deposition method or a spin coating method, deposition conditions and coating conditions may differ according to a compound selected for preparing a target layer, but may be similar to those described with reference to the HIL. An ETL material may stably transport electrons injected from an electron injection electrode (cathode), and may be any known electron transporting material. For example, the ETL may be a quinoline derivative such as tris(8-quinolinolate)aluminum ($Alq_3$), TAZ, Balq, or beryllium bis benzoquinolin-10-olate ($Bebq_2$), but is not limited thereto. Exemplary compounds are shown below:

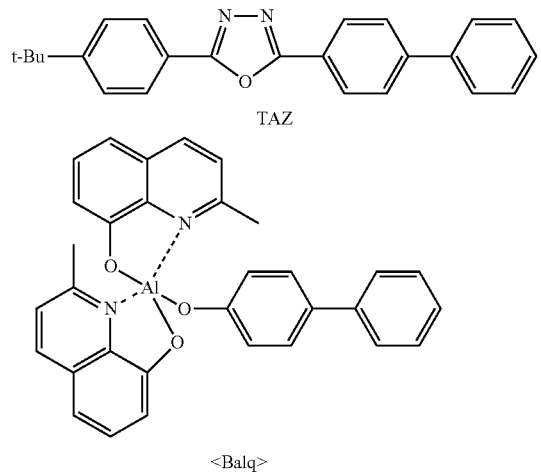

<TAZ>

<Balq>

The thickness of the ETL may be from about 100 Å to about 1000 Å, for example, from about 150 Å to about 500 Å. If the thickness of the ETL is within this range, excellent electron transporting characteristics may be obtained without a substantial increase in the driving voltage of the organic light emitting diode.

In addition, the electron injection layer (EIL) may be formed on the ETL. The EIL may include an EIL material that allows electrons to be easily injected from a cathode, and the EIL material may not be particularly limited.

The EIL material may be any known EIL material such as LiF, NaCl, CsF, $Li_2O$, or BaO. Deposition conditions for forming the EIL may differ according to a compound selected for preparing a target layer, and may be similar to those described with reference to the HIL.

The thickness of the EIL may be from about 1 Å to about 100 Å, for example, from about 3 Å to about 90 Å. If the thickness of the EIL is within this range, excellent electron injection characteristics may be obtained without a substantial increase in the driving voltage of the organic light emitting diode.

The second electrode 17 may be formed on the organic layer 15. The second electrode 17 may be a transmissive electrode. The second electrode 17 may be a cathode that is an electron injection electrode. When the second electrode 17 is a cathode, the second electrode 17 may be manufactured using a metal, an alloy, an electrically conductive compound, or a mixture thereof, each of which has a low work function constant, such as lithium (Li), magnesium (Mg), aluminum (Al), aluminum-lithium (Al—Li), potassium (K), magnesium-indium (Mg—In), or magnesium-silver (Mg—Ag). In addition, for a top emission type light emitting diode, the second electrode 17 may be a transmissive electrode including ITO or IZO.

Hereinafter, an organic light emitting diode according to an embodiment will be described in detail with reference to examples. These examples are for illustrative purposes only and are not intended to limit the scope of the present embodiments.

EXAMPLES

Synthesis Example 1

Synthesis of Compound 1

1-1) Synthesis of 2-bromoanthraquinone 200 g (0.896 mol) of 2-aminoanthraquinone, 240.13 g (1.075 mol) of $CuBr_2$, 4 L of acetonitrile, and 138.58 g (1.344 mol) of t-butylnitrite were loaded into a 10 L reactor and then the temperature was increased to 65° C. After 3-hour reaction, the temperature was decreased to room temperature and then 3 L of 2N HCl was added thereto, thereby producing a solid. The solid was filtered and washed with 10 L of water, thereby producing a dark brown solid (203 g, 89%).

1-2) Synthesis of 2-bromo-9,10-diphenylanthracene 164 g (1.045 mol) of bromobenzene was loaded into a 2 L reactor, and then 700 ml of THF was added thereto. The temperature of the reactor was lowered to −78° C., and then 653.06 ml (1.045 mol) of 1.6M n-BuLi was slowly added dropwise thereto.

Then, the mixture was stirred for about one hour at low temperature and then, 100 g (0.348 mol) of 2-bromoanthraquinone obtained from 1-1) was added thereto. The resultant mixture was reacted at room temperature for 6 hours and then 200 ml of 2N HCl was added thereto. The reaction mixture was subjected to layer isolation and an organic solvent included in an organic layer was removed under reduced pressure, thereby obtaining intermediate A. Intermediate A, 173.45 g (1.045 mol) of KI, 221.50 g (2.090 mol) of sodium hyphophosphite, and 1000 ml of AcOH were added to a 2 L reactor and refluxed for 3 hours. The resultant product was cooled to room temperature, thereby producing a solid. The solid was filtered and washed with methanol and water, and then, re-crystallized with toluene, thereby producing a brown solid (105 g, 73%).

1-3) Synthesis of 9,10-diphenylanthracene-2-boronic acid 10 g (0.024 mol) of 2-bromo-9,10-diphenylanthracene obtained from 1-2) and 100 ml of THF were loaded into a 500 ml reactor. Then, the temperature of the reactor was lowered to −78° C. and 16.80 ml (0.027 mol) of 1.6M n-BuLi was slowly added dropwise thereto. Then, the mixture was stirred for about one hour at low temperature and then 3.84 g (0.037 mol) of trimethylborate was added dropwise thereto. Then, the resultant mixture was stirred at room temperature for 4 hours and then 10 ml of 2N HCl was added thereto. Then, 100 ml of EA (ethyl acetate) was added to the obtained mixture and extracted twice with $EA/H_2O$, and an organic solvent was removed under reduced pressure. The obtained product was re-crystallized with EA/Hx (hexane), thereby producing a yellowish white crystal (6 g, 66%).

1-4) Synthesis of 2-(2-nitrophenyl)-9,10-diphenylanthracene 4 g (0.0107 mol) of 9,10-diphenylanthracene-2-boronic acid obtained from 1-3), 1.8 g (0.009 mol) of 2-bromonitrobenzene, 0.2 g (0.17 mmol) of Pd(PPh$_3$)$_4$, 2.5 g (0.018 mol) of K$_2$CO$_3$, 30 ml of THF, 30 ml of 1,4-dioxane, and 10 ml of H$_2$O were loaded into a reactor and then the mixture was refluxed for 12 hours. The resultant product was cooled to room temperature and then subjected to layer isolation and an organic solvent included in an organic layer was removed under reduced pressure, thereby producing a solid. The solid was washed with 100 ml of water and 100 ml of methanol, and then column separation (methylene chloride (MC):hexane (Hx)=1:9) was performed thereon, thereby obtaining a yellow solid (3 g, 75%).

1-5) Synthesis of 6,11-diphenyl-12-H-12-aza indeno[1,2-b]anthracene 21 g (0.0571 mol) of 2-(2-nitrophenyl)-9,10-diphenylanthracene obtained from 1-4), 42.5 g (0.1714 mol) of PPh$_3$, 150 ml of dichlorobenzene were loaded into a 500 ml reactor and then refluxed for 10 hours. After the reaction was terminated, the reaction solution was poured into a 1 L beaker and then heated until the amount of dichlorobenzene was reduced to be half of its initial amount. The resultant mixture was cooled to room temperature and then 500 ml of methanol was added thereto to precipitate a solid. The solid was filtered and then dissolved with 150 ml of toluene while heating. Then, the resultant solution was filtered through a Buchner funnel containing celite and silica gel. The filtrate was removed under reduced pressure and then re-crystallization was performed with toluene and methanol, thereby producing a yellow solid (18 g, 92%).

1-6) Synthesis of 6,11-diphenyl-12-methyl-12-aza indeno[1,2-b]anthracene (Compound 1)

2 g (4.77 mmol) of 6,11-diphenyl-12-H-12-aza indeno[1,2-b]anthracene obtained from 1-5) was dissolved in 30 ml of THF in a 100 ml reactor, and then 1 g (9.5 mmol) of Na(t-BuO) was added thereto. 1.4 g (9.5 mmol) of Iodomethane was slowly added dropwise to the obtained mixture for 20 minutes. Then, the resultant mixture was stirred at room temperature for 30 minutes and then an organic solvent was removed under reduced pressure, thereby producing a solid.

The solid was dissolved in toluene and then filtered through a Buchner funnel containing celite and silica gel. The filtrate was removed under reduced pressure and then re-crystallization was performed with toluene, thereby producing a yellow solid (1.4 g, 67%).

Mp 272.15° C.

1H NMR (CDCl3, 300 Mhz), δ8.320 (d, 1H), δ8.078 (d, 1H), δ7.933 (d, 1H), δ7.74~7.265 (m, 17H)

Compound 1

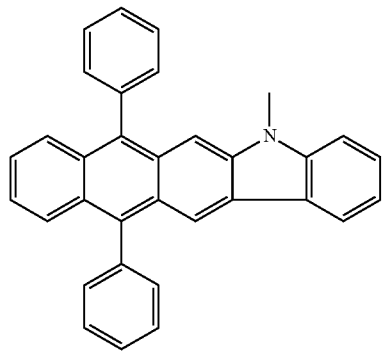

Synthesis Example 2

Synthesis of Compound 8

2-1) Synthesis of 2,6-dibromoanthraquinone 198.2 g (1.5 mol) of tert-butylnitrite and 279.1 g (1.2 mol) of Cu(II)Br were diluted with 6000 ml of acetonitrile in a 10 L flask, and then the temperature was increased to 65° C. and 119.1 g (0.5 mol) of 2,6-diaminoanthraquinone was slowly added thereto for 5 minutes. When formation of N$_2$ gas stopped, the temperature was lowered to room temperature and then 3.6 L of 2N HCl (aq) was added thereto and then stirred, thereby producing a solid. The solid was filtered and washed with excess water, MeOH, and acetone and then dried, thereby producing 2,6-dibromoanthraquinone (180 g, 98.4%) (2,6-dibromoanthraquinone).

2-2) Synthesis of 2,6-dibromo-9,10-diphenylanthracene 128.7 g (0.82 mol) of bromobenzene was dissolved with THF in a 5 L flask and the temperature was lowered to −78° C. and 426 ml (0.68 mol) of 1.6M n-BuLi was slowly added dropwise thereto. The mixture was stirred for one hour and 100 g (0.27 mol) of 2,6-dibromoanthraquinone obtained from 2-1) was slowly added thereto in a solid state and then the temperature was slowly increased to room temperature and the resultant mixture was stirred. After 12 hours, 500 ml of 2N HCl (aq) was added thereto and an organic layer was isolated and dried over MgSO$_4$ and subjected to be under reduced pressure, thereby producing Compound B. The Compound B was used in the subsequent reaction without purification. Compound B, 136.0 g (0.82 mol) of KI, and 173.7 g (1.64 mol) of NaH$_2$PO$_2$.H$_2$O were diluted with an acetic acid and refluxed while heating. The obtained mixture was cooled to room temperature, thereby producing a solid. The solid was filtered and washed with excess water and MeOH. The resultant solid was re-crystallized with 300 ml of toluene and 2,6-dibromo-9,10-diphenylanthracene (100 g, 75%) was obtained.

2-3) Synthesis of nitrophenyl-2-boronic acid 70 g (0.28 mol) of 2-iodonitrobenzene was dissolved with 600 ml of THF in a 1 L flask and the temperature was lowered to −78° C., and then 154.6 ml (309 mol) of 2M PhMgCl was slowly added dropwise thereto. After 30 minutes, 35.0 g (337.2 mol) of B(OCH$_3$)$_3$ was slowly added dropwise thereto, the temperature was raised to room temperature and then the resultant mixture was stirred. 280 ml of 2N HCl(aq) was added to the obtained mixture at a temperature of 0° C. and then, the mixture was extracted using EA and an organic layer was dried over MgSO$_4$ and condensed under reduced pressure, thereby producing a solid. The solid was mixed with hexane to produce slurry and the slurry was filtered to produce nitrophenyl-2-boronic acid (41 g, 87%).

2-4) Synthesis of 2,6-(2-nitrophenyl)-9,10-diphenylanthracene 30 g (61.4 mmol) of 2,6-dibromo-9,10-diphenylanthracene obtained from 2-2), 25.6 g (153.6 mmol) of nitrophenyl-2-boronic acid obtained from 2-3), 3.5 g (0.05 mmol) of Pd(PPh$_3$)$_4$, and 33.9 g (245.8 mmol) of K$_2$CO$_3$ were diluted with 90 ml of dioxane, 90 ml of THF, and 30 ml of H$_2$O and then, the mixture was refluxed while heating. After four days, a solvent was removed and then the resultant mixture was extracted using MC and washed with a saturated NaCl solution. Then, an organic layer was dried and condensed over MgSO$_4$, and then purification was performed by column chromatography (MC/Hex=1/4), thereby producing 2,6-(2-nitrophenyl)-9,10-diphenylanthracene (8.5 g, 24%) that was yellow solid.

2-5) Synthesis of 8-H,6-H-8,6-diaza diindeno[1,2-b],[1',2'-i]anthracene 8.5 g (14.8 mmol) of 2,6-(2-nitrophenyl)-9,10-diphenylanthracene obtained from 2-4) was dissolved with 80 ml of 1,2-dichlorobenzene in a 250 ml flask, and then 37.1 g (72.2 mmol) of PPh$_3$ was added thereto and the mixture was refluxed while heating. After 12 hours, a solvent was removed, and purification was performed by column chromatography (MC/Hex=1/10) to obtain 8-H,6-H-8,6-diaza diindeno[1,2-b],[1',2'-i]anthracene (7.5 g, 98%) that was colorless.

2-6) Synthesis of 8,6-dimethyl-8,6-diaza diindeno[1,2-b],[1',2'-i]anthracene (Compound 8)

7.7 g (15.2 mmol) of 8-H,6-H-8,6-diaza diindeno[1,2-b],[1',2'-i]anthracene was dissolved with 70 ml of THF in a 250 ml flask, and 3.6 g (38.1 mmol) of t-BuONa was added thereto and then, CH$_3$I was slowly added thereto at room temperature. After 30 minutes, a solvent was removed to obtain a solid. The solid was hot filtered twice using dichlorobenzene, and also re-crystallized using pyridine once. Then, the resultant product was dried under reduced pressure to obtain 8,6-dimethyl-8,6-diaza diindeno[1,2-b],[1',2'-i]anthracene (4.9, 60%) that was white yellow.

Mp=298° C.

1H NMR (300 MHz, CDCl3) δ 2.92 (6H, d), 7.24~7.66 (14H, m), 7.86 (2H, s), 7.98 (2H, d), 8.14 (4H, m)

Compound 8

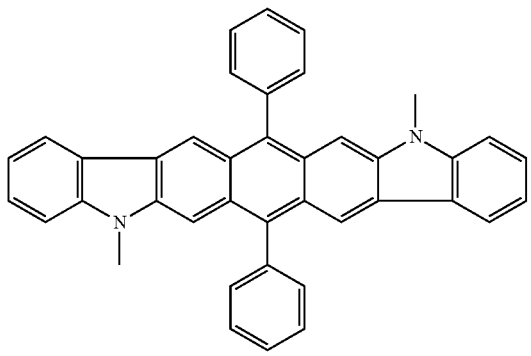

Synthesis Example 3

Synthesis of Compound 16

3-1) Synthesis of 2-bromo-9,10-di(naphthyl)anthracene 360 g (1.74 mol) of bromonaphthalene was dissolved with THF in a 5 L flask and the temperature was lowered to −78° C. and 1600 ml (1.6 mol) of 1.6M n-BuLi was slowly added dropwise thereto. The mixture was stirred for one hour, and then 200 g (0.68 mol) of 2-bromoanthraquinone was added thereto in a solid state and then the temperature was slowly raised to room temperature and the resultant mixture was stirred. After 12 hours, 500 ml of 2N HCl(aq) was added thereto. Then, an organic layer was isolated and dried over MgSO$_4$ and condensed under reduced pressure, thereby producing Compound C. The Compound C was used in the subsequent reaction without purification. Compound C, 346 g (2.09 mol) of KI, and 443 g (4.1 mol) of NaH$_2$PO$_2$.H$_2$O were diluted with an acetic acid and then the mixture was refluxed while heating. The temperature was lowered to room temperature and thus a solid was precipitated. The solid was filtered, washed with excess water and MeOH, and re-crystallized with 300 ml of toluene, thereby producing 2-bromo-9,10-di(2-naphthyl)anthracene (230 g, 64%).

3-2) Synthesis of 2-bromo-9,10-di(2-naphthyl)anthracene 190 g (0.37 mol) of 2-bromo-9,10-di(2-naphthyl)anthracene obtained from 3-1) was dissolved with 1.5 L of THF in a 5 L flask and the temperature was cooled to −78° C. Then, 279 ml (0.44 mol) of 1.6 M n-BuLi was slowly added dropwise thereto. After one hour, 140 g (0.74 mol) of B(OiPr)$_3$ was slowly added dropwise thereto and the temperature was raised to room temperature and the mixture was stirred. 1 L of 2N HCl(aq) was added to the resultant mixture at a temperature of 0° C. and then the mixture was extracted using EA. An organic layer was dried over MgSO$_4$ and then re-crystallized with EA/hexane, thereby producing 2-bromo-9,10-di(2-naphthyl)anthracene (150 g, 84%).

3-3) Synthesis of 2-(2-nitrophenyl)-9,10-di(2-naphthyl)anthracene 10 g (21.1 mmol) of 9,10-dinaphthylanthracene-2-boronic acid, 10.64 g (52.7 mmol) of bromonitrobenzene, 1.21 g (0.05 mmol) of Pd(PPh$_3$)$_4$, and 11.65 g (84.3 mmol) of K$_2$CO$_3$ were diluted with 100 ml of dioxane, 100 ml of THF, and 30 ml of H$_2$O, and then, the mixture was refluxed while heating. After 12 hours, a solvent was removed and the resultant mixture was extracted using MC and washed with a saturated NaCl solution. Then, an organic layer was dried and condensed over MgSO$_4$, and the obtained product was purified by column chromatography (MC/Hex=1/5), thereby producing 2-(2-nitrophenyl)-9,10-di(2-naphthyl)anthracene that was yellow solid (8.4 g, 73%).

3-4) Synthesis of 6,11-di(2-naphthyl)-12-H-12-aza-indeno[1,2-b]anthracene 8.4 g (15.2 mmol) of 2-(2-nitrophenyl)-9,10-di(2-naphthyl)anthracene obtained from 3-3) was dissolved in 80 ml of 1,2-dichlorobenzene in a 250 ml flask and then 45.6 mmol (22.8 g) of PPh$_3$ was added thereto, and the mixture was refluxed while heating. After 12 hours, a solvent was removed and the resultant mixture was purified by column chromatography (MC/Hex=1/10), thereby producing 6,11-di(2-naphthyl)-12-H-12-aza-indeno[1,2-b]anthracene (7.4 g, 96%) that was a colorless solid.

3-5) Synthesis of 6,11-di(2-naphthyl)-12-methyl-12-aza indeno[1,2-b]anthracene (Compound 16)

7.4 g (14.2 mmol) of 6,11-di(2-naphthyl)-12-H-12-aza-indeno[1,2-b]anthracene was dissolved with 70 ml of THF in a 250 ml flask, and 1.64 g (17.0 mmol) of t-BuONa was added thereto and then, 2.4 ml (17.0 mmol) of CH$_3$I was slowly added thereto at room temperature. After 30 minutes, a solvent was removed to obtain a solid, and the solid was hot filtered twice using dichlorobenzene, and re-crystallized three times using dichlorobenzene. Then, the resultant solid was dried under reduced pressure, thereby producing 6,11-di (2-naphthyl)-12-methyl-12-aza indeno[1,2-b]anthracene (3.5 g, 46%) that was white yellow.

Mp=274° C.

1H NMR (300 MHz; CDCl3) δ 2.87 (3H, 2), 7.28~8.34 (24H, m)

Compound 16

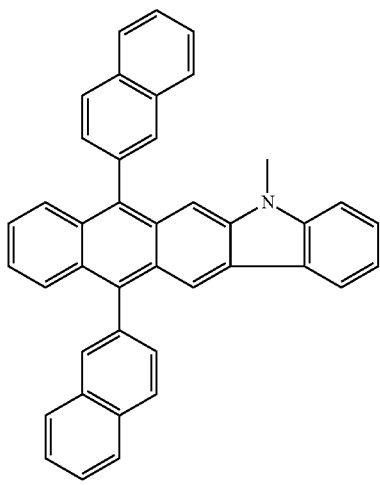

Example 1

An ITO layer on a substrate was patterned such that a light emitting area had a size of 2 mm×2 mm, and then washed. The substrate including the patterned ITO layer was loaded into a vacuum chamber and then, a base pressure was controlled to be 1×10$^{-6}$ torr. Then, a DNTPD layer (700 Å), an NPD layer (300 Å), a layer including AND (host) and Compound 1 (dopant: 3 weight %) (250 Å), a Bebq2 layer (250 Å), a LiF layer (5 Å), and an Al layer (700 Å) were sequentially formed on the ITO layer on the substrate in this stated order, thereby manufacturing an organic light emitting diode.

Example 2

An organic light emitting diode was manufactured in the same manner as in Example 1, except that Compound 8 was used instead of Compound 1.

Example 3

An organic light emitting diode was manufactured in the same manner as in Example 1, except that Compound 16 was used instead of Compound 1.

Evaluation Example

The driving voltage, current at the driving voltage, current density, brightness, electric power, quantum efficiency, and efficiency of the organic light emitting diodes manufactured according to Examples 1 to 3 were evaluated using a PR650 (Spectroscan) Source Measurement Unit. (Manufacturer: PhotoResearch Co., Chatworth, Calif.). The results are shown in Table 1 below.

TABLE 1

|  | Example 1 | Example 2 | Example 3 |
|---|---|---|---|
| Driving voltage (V) | 6.03 | 5.49 | 5.52 |
| Current at the driving voltage (A) | 0.0004 | 0.0004 | 0.0004 |
| Current density (mA/cm2) | 10 | 10 | 10 |
| Brightness (Cd/A) | 11.22 | 1.56 | 13.17 |
| Electric power (lm/W) | 5.84 | 6.04 | 7.49 |
| Quantum efficiency (Q.E) | 5.43 | 4.23 | 5.62 |
| Efficiency (Cd/m$^2$)(magnification) | 1122 | 1056 | 1317 |

As described above, an organic light emitting diode having an organic layer including the condensed-cyclic compound of Formula 1 has low driving voltage, high current density, high luminosity, high quantum efficiency, high efficiency.

While the present embodiments have been particularly shown and described with reference to exemplary embodiments thereof, it will be understood by those of ordinary skill in the art that various changes in form and details may be made therein without departing from the spirit and scope of the present embodiments as described by the following claims.

What is claimed is:

1. A condensed-cyclic compound represented by any one of the following Formulae:

Formula 1b-1

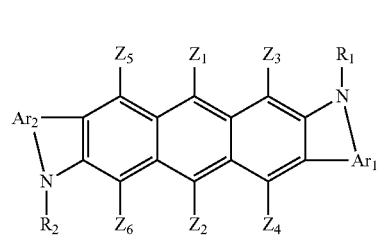

Formula 1h-1

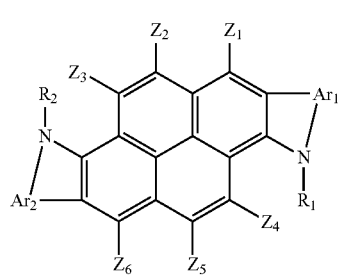

Formula 1a-2

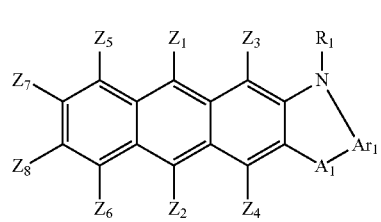

Formula 1b-2
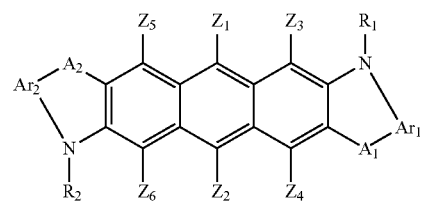

Formula 1g-2
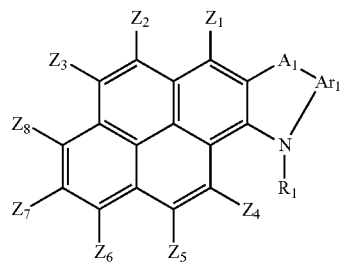

Formula 1h-2
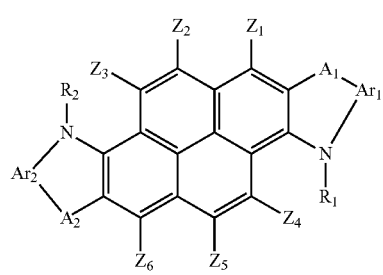

Formula 2b-1
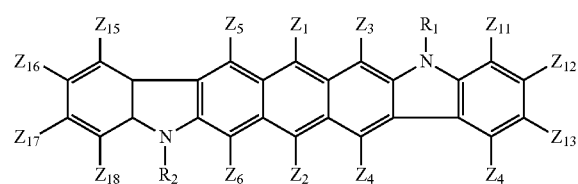

Formula 2h-1
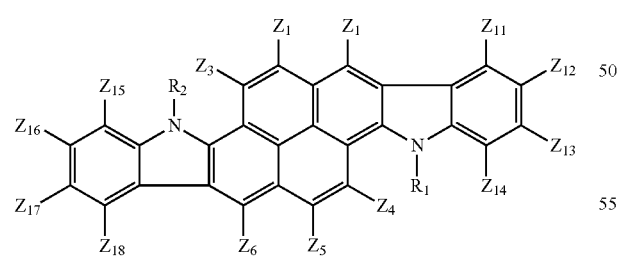

Formula 2a-2
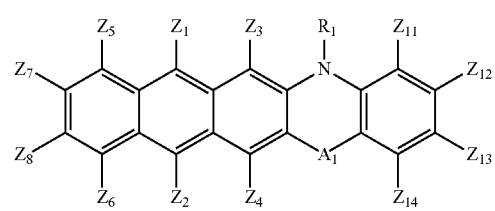

Formula 2b-2
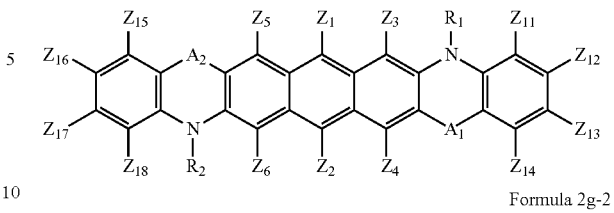

Formula 2g-2
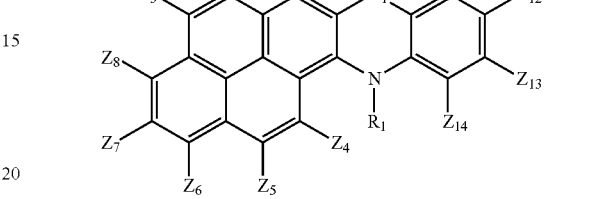

Formula 2h-2
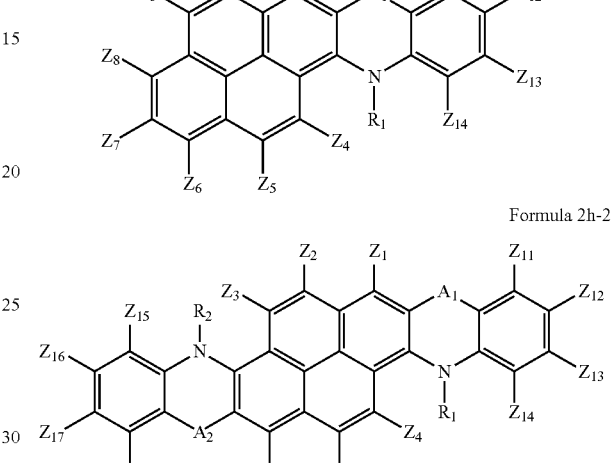

Formula 3a-2
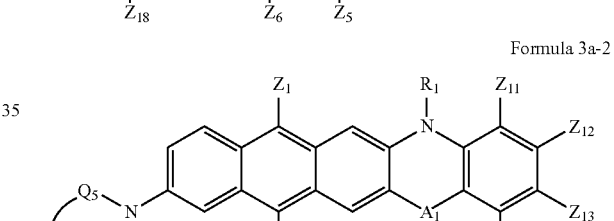

Formula 3g-2
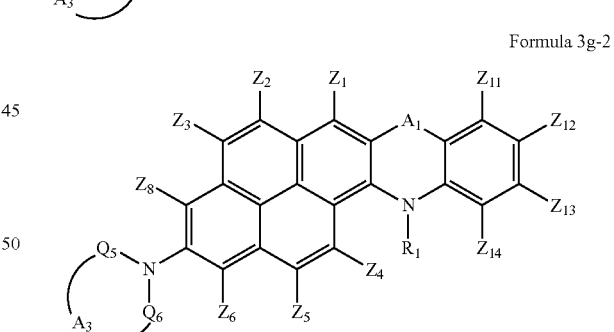

wherein $Ar_1$ and $Ar_2$ are, each independently, selected from the group consisting of a substituted or unsubstituted $C_6$-$C_{16}$ arylene group, and a substituted or unsubstituted $C_3$-$C_{16}$ heteroarylene group;

$A_1$ and $A_2$ are, each independently, a divalent linking group represented by $-[C(Q_1)(Q_2)]_q-$ where $Q_1$ and $Q_2$ are, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group, and q is an integer from 1 to 3;

$A_3$ is a single bond or a $C_1$-$C_3$ alkylene group;

$R_1$ and $R_2$ are, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, an unsubstituted $C_6$ aryl group, an unsubstituted $C_{10}$-$C_{16}$ fused aryl group, a substituted or unsubstituted $C_3$-$C_{16}$ heteroaryl group, and a group represented by —N($Q_3$)($Q_4$), wherein $Q_3$ and $Q_4$ are, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group, and $Q_3$ and $Q_4$ optionally are selectively fused with each other, or linked to each other by a single bond, a double bond, or a $C_1$-$C_3$ alkylene group, thereby forming a saturated or unsaturated ring; and $Z_1$ to $Z_{18}$ are, each independently, selected from the group consisting of a hydrogen atom, a heavy hydrogen atom, a halogen atom, a hydroxyl group, a cyano group, a substituted or unsubstituted $C1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group, and wherein $Q_5$ and $Q_6$ are, each independently, selected from the group consisting of a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group.

2. The condensed-cyclic compound of claim 1, wherein $Ar_1$ and $Ar_2$ are, each independently selected from the group consisting of a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted benzofuranylene group, a substituted or unsubstituted thiophenylene group, a substituted or unsubstituted benzothiophenylene group, a substituted or unsubstituted isothiazolylene group, and a substituted or unsubstituted isoxazolylene group.

3. The condensed-cyclic compound of claim 1, wherein $Ar_1$ and $Ar_2$ are, each independently selected from the group consisting of a substituted or unsubstituted phenylene group, a substituted or unsubstituted naphthylene group, and a substituted or unsubstituted anthracenylene group.

4. The condensed-cyclic compound of claim 1, wherein $Q_1$ and $Q_2$ are each independently selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group.

5. The condensed-cyclic compound of claim 1, wherein q is 0.

6. The condensed-cyclic compound of claim 1, wherein q is an integer from 1 to 3.

7. The condensed-cyclic compound of claim 1, wherein $R_1$ and $R_2$ are each independently selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, an unsubstituted $C_6$ aryl group, an unsubstituted $C_{10}$-$C_{16}$ fused aryl group, a substituted or unsubstituted $C_3$-$C_{16}$ heteroaryl group, and a group represented by —N($Q_3$)($Q_4$); wherein $Q_3$ and $Q_4$ are, each independently, selected from the group consisting of a hydrogen atom, a heavy hydrogen atom, a halogen atom, a hydroxyl group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{16}$ aryl group, and a substituted or unsubstituted $C_3$-$C_{16}$ heteroaryl group, and wherein $Q_3$ and $Q_4$ are optionally fused with each other, or linked to each other by a single bond, a double bond, or a $C_1$-$C_3$ alkylene group.

8. The condensed-cyclic compound of claim 1, wherein q is 2.

9. The condensed-cyclic compound of claim 1, wherein q is 1.

10. The condensed-cyclic compound of claim 1, wherein the condensed-cyclic compound is represented by any one of Formulas 1b-1 and 1h-1:

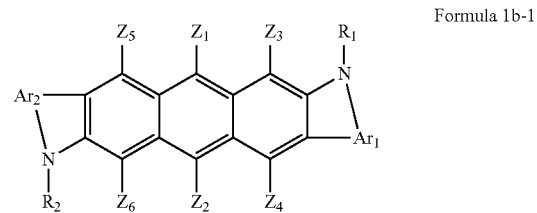

Formula 1b-1

-continued

Formula 1h-1

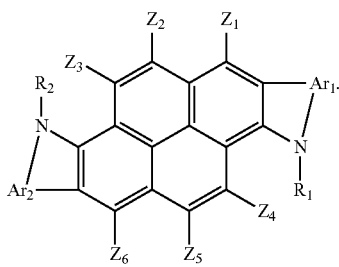

11. The condensed-cyclic compound of claim 1, wherein the condensed-cyclic compound is represented by any one of Formulas 1a-2 to 1h-2:

Formula 1a-2

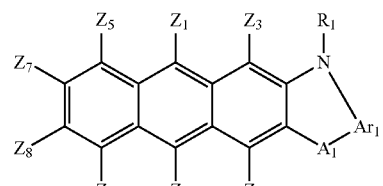

Formula 1b-2

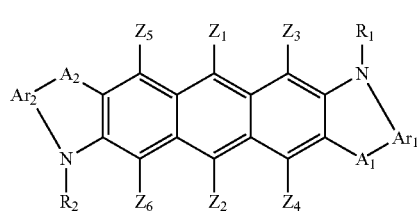

Formula 1g-2

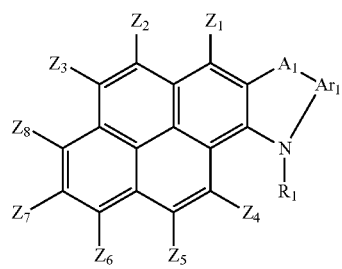

Formula 1h-2

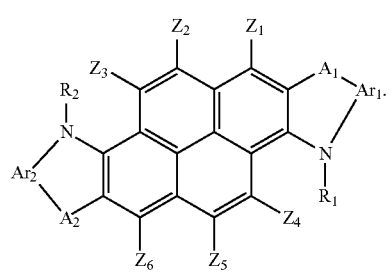

12. The condensed-cyclic compound of claim 1, wherein the condensed-cyclic compound is represented by any one of Formulas 2b-1 and 2h-1:

Formula 2b-1

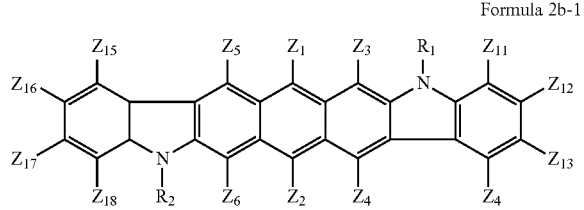

Formula 2h-1

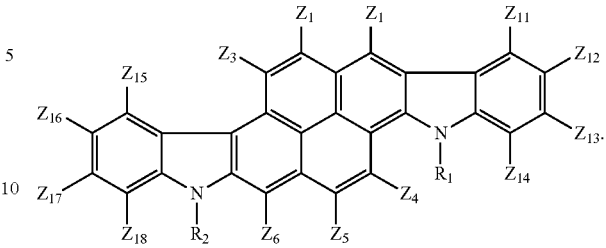

13. The condensed-cyclic compound of claim 1, wherein the condensed-cyclic compound is represented by any one of Formulas 2a-2 to 2h-2:

Formula 2a-2

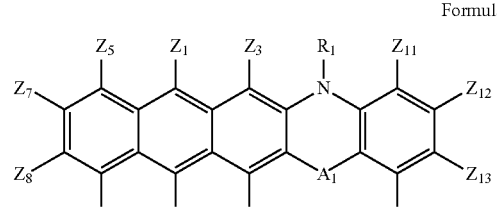

Formula 2b-2

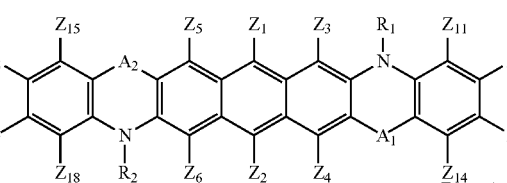

Formula 2g-2

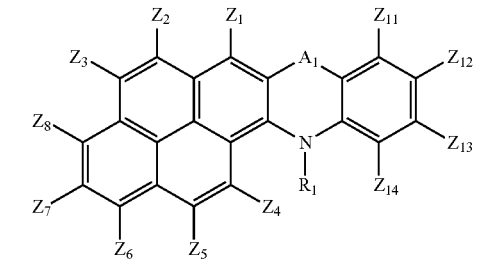

Formula 2h-2

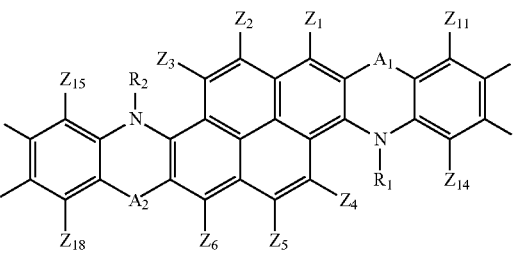

14. The condensed-cyclic compound of claim 1, wherein the condensed-cyclic compound is represented by Formula 3a-2, 3c-1, 3c-2, 3e-1, 3e-2, or 3g-2:

Formula 3a-2

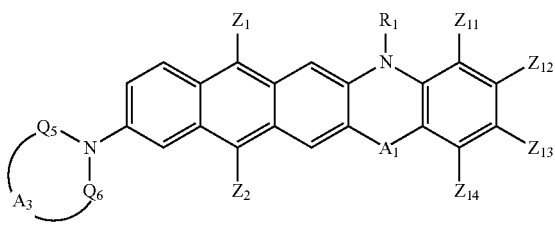

-continued

Formula 3g-2

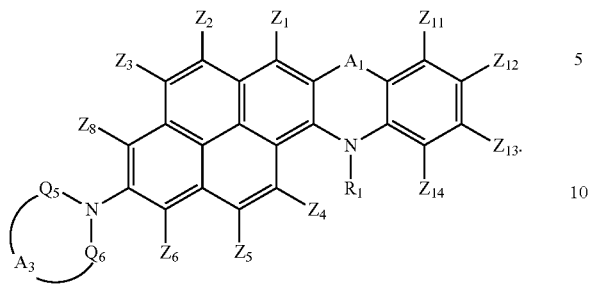

15. An organic light emitting diode comprising: a first electrode, a second electrode facing the first electrode, and an organic layer interposed between the first electrode and the second electrode, wherein the organic layer comprises the condensed-cyclic compound of claim 1.

16. The organic light emitting diode of claim 15, wherein the organic layer comprises a light emitting layer.

17. The organic light emitting diode of claim 16, wherein the light emitting layer further comprises a host.

* * * * *